(12) United States Patent
Sommer et al.

(10) Patent No.: US 7,978,814 B2
(45) Date of Patent: *Jul. 12, 2011

(54) HIGH SPEED MATERIALS SORTING USING X-RAY FLUORESCENCE

(75) Inventors: Edward J. Sommer, Nashville, TN (US); Robert H. Parrish, Nashville, TN (US); David B. Spencer, Bedford, MA (US); Charles E. Roos, Nashville, TN (US)

(73) Assignee: Spectramet, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/605,623

(22) Filed: Oct. 26, 2009

(65) Prior Publication Data

US 2010/0111252 A1     May 6, 2010

Related U.S. Application Data

(63) Continuation of application No. 12/138,927, filed on Jun. 13, 2008, now Pat. No. 7,616,733, which is a continuation of application No. 11/357,432, filed on Feb. 17, 2006, now abandoned, which is a continuation of application No. 11/232,574, filed on Sep. 22, 2005, now abandoned, which is a continuation of application No. 10/967,981, filed on Oct. 19, 2004, now abandoned, which is a continuation of application No. 10/364,783, filed on Feb. 11, 2003, now Pat. No. 6,888,917, which is a continuation of application No. 09/827,784, filed on Apr. 6, 2001, now Pat. No. 6,519,315, which is a continuation of application No. 09/400,491, filed on Sep. 21, 1999, now Pat. No. 6,266,390.

(60) Provisional application No. 60/101,128, filed on Sep. 21, 1998.

(51) Int. Cl.
*G01N 23/223* (2006.01)
*G01N 23/04* (2006.01)

(52) U.S. Cl. ............................. 378/45; 378/44; 378/57
(58) Field of Classification Search .................. 378/44, 378/45, 57
See application file for complete search history.

(56) References Cited

U.S. PATENT DOCUMENTS 5,314,072 A * 5/1994 Frankel et al. ............... 209/44.1
5,339,962 A * 8/1994 Sommer et al. .............. 209/576

* cited by examiner

*Primary Examiner* — Irakli Kiknadze
(74) *Attorney, Agent, or Firm* — Wolf, Greenfield & Sacks, P.C.

(57) ABSTRACT

A system and process for classifying a piece of material of unknown composition at high speeds, where the system connected to a power supply. The piece is irradiated with first x-rays from an x-ray source, causing the piece to fluoresce x-rays. The fluoresced x-rays are detected with an x-ray detector, and the piece of material is classified from the detected fluoresced x-rays. Detecting and classifying may be cumulatively performed in less than one second. An x-ray fluorescence spectrum of the piece of material may be determined from the detected fluoresced x-rays, and the detection of the fluoresced x-rays may be conditioned such that accurate determination of the x-ray fluorescence spectrum is not significantly compromised, slowed or complicated by extraneous x-rays. The piece of material may be classified by recognizing the spectral pattern of the determined x-ray fluorescence spectrum. The piece of material may be flattened prior to irradiation and detection. The x-ray source may irradiate the first x-rays at a high intensity, and the x-ray source may be an x-ray tube.

18 Claims, 10 Drawing Sheets

HIGH SPEED MATERIALS SORTING USING X-RAY FLUORESCENCE

RELATED APPLICATION

This application is a continuation, claiming the benefit under 35 U.S.C. §120, of U.S. application Ser. No. 12/138,927, titled "High Speed Materials Sorting Using X-Ray Fluorescence", filed Jun. 13, 2008, currently pending, which is a continuation of U.S. application Ser. No. 11/357,432, titled "High Speed Materials Sorting Using X-ray Fluorescence", filed Feb. 17, 2006, now abandoned, which is a continuation of U.S. application Ser. No. 11/232,574, titled "High Speed Materials Sorting Using X-Ray Fluorescence", filed Sep. 22, 2005, now abandoned, which is a continuation of U.S. application Ser. No. 10/967,981, titled "High Speed Materials Sorting Using X-Ray Fluorescence", filed Oct. 19, 2004, now abandoned, which is a continuation of U.S. application Ser. No. 10/364,783, titled "High Speed Materials Sorting Using X-Ray Fluorescence", filed Feb. 11, 2003, issued May 3, 2005 as U.S. Pat. No. 6,888,917, which is a continuation of U.S. patent application Serial no. 09/827,784, titled "High Speed Materials Sorting Using X-Ray Fluorescence", filed Apr. 6, 2001, issued Feb. 11, 2003 as U.S. Pat. No. 6,519,315, which is a continuation of U.S. patent application Ser. No. 09/400,491 titled, "High Speed Materials Sorting Using X-Ray Fluorescence", filed Sep. 21, 1999, issued Jul. 24, 2001 as U.S. Pat. No. 6,266,390, which claims priority under 35 U.S.C. §119(e) to U.S. provisional application Ser. No. 60/101,128 titled, "Electronics Sortation for Recycling of Post Consumer Non-Ferrous Metals," filed Sep. 21, 1998, where each application is hereby incorporated by reference in its entirety.

GOVERNMENT LICENSE RIGHTS

The U.S. Government has a paid-up license in this invention and the right in limited circumstances to require the patent owner to license others on reasonable terms as provided for by the terms of Grant No. DMI-9761412 awarded by the National Science Foundation.

This invention was made with Government support under Grant No. DMI-9761412 awarded by the National Science Foundation. The Government has certain rights in this invention.

FIELD OF THE INVENTION

This invention relates to a system and process for sorting pieces of materials (by composition) in a stream of materials moving along a conveyor belt. Particularly, this invention relates to a system and process for classifying pieces of materials of unknown composition based on the x-ray fluorescence spectrum of each respective piece so as to permit very high speed sorting of the unknown materials.

BACKGROUND OF THE INVENTION

Current worldwide environmental concerns have fueled an increase in efforts to recycle used equipment and articles containing materials that can be reused. Such efforts have produced new and improved processes for sorting materials such as plastics, glass, metals, and metal alloys.

As used herein, a "material" may be a chemical element, a compound or mixture of chemical elements, or a compound or mixture of a compound or mixture of chemical elements, wherein the complexity of a compound or mixture may range from being simple to complex. Materials may include metals (ferrous and non-ferrous), metal alloys, plastics, rubber, glass, ceramics, etc. As used herein, element means a chemical element of the periodic table of elements, including elements that may be discovered after the filing date of this application.

Generally, methods for sorting pieces of materials involve determining a physical property or properties of each piece, and grouping together pieces sharing a common property or properties. Such properties may include color, hue, texture, weight, density, transmissivity to light, sound, or other signals, and reaction to stimuli such as various fields. Methods to determine these properties include visual identification of a material by a person, identification by the amount and/or wavelength of the light waves emitted or transmitted, eddy-current separation, heavy-media plant separation, and x-ray fluorescence detection.

With respect to metals and metal alloys, today it is neither technically nor commercially feasible to separate and recover many of the non-ferrous metals that are manufactured into products and discarded at the end of their useful life. In residential waste, only aluminum cans are recycled to any significant degree. Virtually none of the other non-ferrous materials in our residential waste are recovered. Instead, they are disposed in landfills. Further, small non-ferrous materials below ⅝ inches in size are landfilled from nearly 200 automobile shredders.

Smaller-sized pieces of non-ferrous metals from automobile shredders are not separated because their recovery is not cost-effective. They can only be consolidated and shipped to larger facilities for further processing. Mixed non-ferrous metals from industrial processes are often disposed or junked because hand-sorting and small-particle recovery technologies either do not work well or are not cost-effective. Nearly 2 billion pounds of valuable non-ferrous metals are discarded in landfills every year in the U.S. alone. Worldwide, the amount of metal wasted is far greater. If this metal could be economically recycled at high volumes, the potential value generated is estimated to be in excess of 1 billion dollars (U.S.) per year. Further, there are approximately 200 waste-to-energy facilities, 200 automobile shredders, and thousands of metal scrap yards in the U.S. alone that could benefit financially (and otherwise) from an improved sorting system.

X-ray fluorescence spectroscopy has long been a useful analytical tool in the laboratory for classifying materials by identifying elements within the material, both in academic environments and in industry. The use of characteristic x-rays such as, for example, K-shell or L-shell x-rays, emitted under excitation provides a method for positive identification of elements and their relative amounts present in different materials, such as metals and metal alloys. For example, radiation striking matter causes the emission of characteristic K-shell x-rays when a K-shell electron is knocked out of the K-shell by incoming radiation and is then replaced by an outer shell electron. The outer electron, in dropping to the K-shell energy state, emits x-ray radiation characteristics of the atom.

The energy of emitted x-rays depends on the atomic number of the fluorescing elements. Energy-resolving detectors can detect the different energy levels at which x-rays are fluoresced, and generate an x-ray signal from the detected x-rays. This x-ray signal may then be used to build an energy spectrum of the detected x-rays, and from the information, the element or elements which produced the x-rays may be identified. Fluorescent x-rays are emitted isotopically from an irradiated element and the detected radiation depends on the solid angle subtended by the detector and any absorption of this radiation prior to the radiation reaching the detector. The lower the energy of an x-ray, the shorter the distance it will travel before being absorbed by air. Thus, when detecting x-rays, the amount of x-rays detected is a function of the quantity of x-rays emitted, the energy level of the emitted x-rays, the emitted x-rays absorbed in the transmission medium, the angles between the detected x-rays and the detector, and the distance between the detector and the irradiated material.

Although x-ray spectroscopy is a useful analytical tool for classifying materials, with current technology, the cost is high per analysis, and the time required is typically minutes or hours. Scrap yard identification of metals and alloys is primarily accomplished today by trained sorters who visually examine each metal object one at a time. Contamination is removed by shearing. A trained sorter observes subtle characteristics of color, hue, texture, and density to qualitatively assess the composition of the metal. Sometimes, spark testing or chemical "litmus" testing aids in identification. The process is slow and inaccurate, but is the most common method in existence today for sorting scrap metal to upgrade its value.

There have been disclosed a variety of systems and techniques for classifying materials based on the x-ray fluorescence of the material. Some of these systems involve handheld or bench-top x-ray fluorescence detectors. Some of these systems include serially conveying pieces of material along a conveyor belt and irradiating each piece, in turn, with x-rays. These x-rays cause each piece of material to fluoresce x-rays at various energy levels, depending on the elements contained in the piece. The fluoresced x-rays are detected, and the piece of material is then classified based on the fluoresced x-rays and sorted in accordance with this classification.

Such disclosed systems, however, have not been widely accepted commercially because they require about one second or more to detect the x-rays and accurately classify the piece of material accordingly, and they are expensive relative to the number of objects identified per unit time.

SUMMARY OF THE INVENTION

In response to the need for faster classification, disclosed herein is a system and process for classifying a piece of material based on the x-ray fluorescence of its constituents, wherein x-rays are detected from the piece and the piece is accurately classified, cumulatively, in substantially less than a second—indeed, typically in about 100 milliseconds (ms) or less.

To achieve these speeds, a high intensity x-ray source, such as an x-ray tube, is used to irradiate the piece. The previously mentioned systems, by contrast, employ a comparatively low-power narrow-spectrum x-ray source such as, for example, Cadmium isotope $Cd^{129}$, Americium isotope $Am^{241}$, Cobalt isotope $Co^{57}$, and Iron isotope $Fe^{55}$. Although use of an x-ray tube has been mentioned as a possible alternative x-ray source for a material sorting system, a high intensity x-ray source has not been implemented by others in such systems, and there are major problems in doing so that have not previously been resolved. Consequently, there previously has not been shown a system that enables use of a high intensity x-ray source in such a system.

Another problem with many known material sorting systems that classify pieces of material based on the x-ray fluorescence of the material is that such systems are limited to analyzing only the fluorescence of specific, predetermined elements of interest in the piece of material. Analyzing only select fluorescence limits the accuracy of the identification and the range of materials that can be identified.

In response to this problem, there is also disclosed herein a system and process for classifying a piece of material based on the x-ray fluorescence of the piece by recognizing a broad spectral pattern of the x-ray fluorescence. According to the invention, a high speed process for classifying a piece of material of unknown composition is provided. The piece is irradiated with x-rays from an x-ray source, causing the piece to fluoresce x-rays. The fluoresced x-rays are detected with an x-ray detector and the piece is classified from the detected fluoresced x-rays.

In optional illustrative embodiments, detecting and classifying are cumulatively performed in less than one second, less than 500 ms, less than 100 ms, less than 50 ms, and preferably even less than 15 ms.

Preferably, but optionally, an x-ray fluorescence spectrum of the piece of material from the detected fluoresced x-rays is determined, and at least one of the steps of the irradiating and detecting includes conditioning the irradiating x-rays or the fluoresced x-rays, respectively, such that speed and accuracy of determining the x-ray fluorescence spectrum is not significantly compromised or complicated by generation or detection of extraneous x-rays.

In yet another optional aspect, the irradiating x-rays are filtered to reduce a number of irradiating x-rays having an energy level too low to cause the piece to fluoresce x-rays having an energy level within a predefined range of the x-ray fluorescence spectrum.

In still another optional aspect, the irradiating x-rays are aimed at the piece of material to reduce an amount of x-rays detected by the x-ray detector that were not fluoresced by the piece itself.

In still another optional aspect of the illustrated embodiments, the x-ray fluorescence spectrum is determined for a predefined range of energy levels, and the irradiating x-rays are aimed by collimating the x-ray source with a collimator whose aperture components are made substantially of one or more materials that fluoresce at energy levels not within the predefined range.

For example, the operative parts of the collimator may be formed essentially of polyvinyl chloride.

In another optional aspect, the x-ray source is aimed at the piece of material with a small aperture to substantially confine the x-rays detected by the x-ray detector to those fluoresced by the piece and limit detection of other x-rays.

In another optional aspect, the x-ray detection is aimed by collimating the x-ray detector with a collimator consisting essentially of one or more materials that fluoresce at energy levels not within the predefined range. For example, the collimator may be formed essentially of polyvinyl chloride.

In yet another optional aspect, the piece of material is conveyed on a conveyor through a detection area where the irradiating x-rays irradiate the piece and the fluoresced x-rays are detected from the piece. The conveyor may be formed essentially of one or more materials that fluoresce at energy levels not within the predefined energy range, so that the conveyor does not fluoresce x-rays that significantly interfere with determination of the x-ray fluorescence spectrum of the piece.

In another optional aspect, the spectral pattern of the determined x-ray fluorescence spectrum is recognized.

In still another optional aspect, a plurality of x-ray fluorescence spectra are stored as reference spectra on a computer-readable medium, each reference spectrum having a spectral pattern and corresponding to a different material classification. Recognizing the detected spectral pattern includes comparing the determined x-ray fluorescence spectrum to each of the reference spectra to determine which reference spectrum has a spectral pattern most similar to the spectral pattern of the determined x-ray fluorescence spectrum. The piece of material is classified as the material classification corresponding to the reference spectrum determined to have the most similar spectral pattern.

In a further optional aspect, the piece of material is conveyed on a conveyor and through a detection area where the irradiating x-rays irradiate the piece and the fluoresced x-rays are detected from the piece, and an ejector corresponding to the classification of the piece is actuated such that the piece is ejected from the conveyor at a point downstream from the detection area and associated with said classification.

In another optional aspect, the piece of material is flattened prior to irradiation and detection.

In still another optional aspect, the step of irradiating includes irradiating the x-rays at a high intensity.

Optionally, but preferably, the x-ray source is an x-ray tube.

It will be appreciated that both large and small pieces may be processed, including pieces having a largest dimension less than 5/8 inch; indeed, even less than approximately 1/4 inch.

In another illustrative embodiment, a system for classifying a piece of material of unknown composition is provided, where the system is connected to a power supply. An x-ray source powered by the power supply generates x-rays that irradiate the piece of material, causing the piece to fluoresce x-rays. An x-ray detector detects the fluoresced x-rays and produces as an output a signal, called an x-ray signal, representing the detected x-rays. An x-ray fluorescence processing module is connected to the x-ray detector. The processing module receives as an input the x-ray signal and generates as an output a classification signal that identifies the classification of the piece of material.

In optional aspects, the x-ray detector and x-ray fluorescence processing module are operative to detect the fluoresced x-rays and classify the piece, respectively, in a combined time less than one second, less than 500 ms, less than 100 ms, less than 50 ms, and preferably even less than 15 ms.

In yet another optional aspect, the x-ray fluorescence processing module includes a spectrum acquisition module connected to the x-ray detector, the spectrum acquisition module receives as an input the x-ray signal and generates as an output an x-ray fluorescence spectrum, and a classification module receives as an input the x-ray fluorescence spectrum and generates as an output a classification signal indicating a classification of the piece of material. The system is conditioned such that accurate determination of the x-ray fluorescence spectrum is not significantly compromised or complicated by generation or detection of extraneous x-rays.

In another optional aspect of this embodiment, the x-ray fluorescence spectrum is determined for a predefined range of energy levels, and an x-ray filter filters the irradiating x-rays to reduce a number of irradiating x-rays having an energy level too low to cause the piece to fluoresce x-rays having an energy level within the predefined range of the x-ray fluorescence spectrum.

In another optional aspect the output of the x-ray source is conditioned by a collimator, the collimator having an aperture to aim the irradiating x-rays at the piece such that production of x-rays from objects other than the piece is reduced.

In an optional feature of this aspect, the x-ray fluorescence spectrum is determined for a predefined range of energy levels, aperture components of the collimator being made substantially of one or more materials that fluoresce at energy levels not within the predefined range.

For example, the collimator may be formed essentially of polyvinyl chloride.

In another optional aspect, the x-rays detected by the x-ray detector are conditioned by a collimator, the collimator having an aperture to aim the detection of the fluoresced x-rays at the piece during the detection such that detection of incident radiation from objects other than the piece is minimized.

For example, the collimator may be formed essentially of polyvinyl chloride.

In still another optional aspect, the x-ray fluorescence spectrum is determined for a predefined range of energy levels, and a conveyor conveys the piece of material through a detection area where the irradiating x-rays irradiate the piece and the fluoresced x-rays are detected from the piece, and the conveyor consists essentially of one or more materials that fluoresce at energy levels not within the predefined range.

For example, the conveyor belt may be formed essentially of polyvinyl chloride.

In another optional aspect, the x-ray fluorescence processing module includes a spectrum acquisition module connected to the x-ray detector, the spectrum acquisition module to receive as an input the x-ray signal and to generate as an output an x-ray fluorescence spectrum, and a classification module to receive as an input the x-ray fluorescence spectrum and to generate as an output a classification signal that indicates the classification of the piece, wherein the classification module is operative to classify the piece by recognizing a spectral pattern of the x-ray fluorescence spectrum.

In yet another optional aspect, a computer-readable storage medium stores a plurality of x-ray fluorescence spectra as reference spectra, each reference spectrum having a spectral pattern and corresponding to a different material classification, and the classification module further includes means for comparing the determined x-ray fluorescence spectrum to each of the reference spectra to determine which reference spectrum has a spectral pattern most similar to the spectral pattern of the determined x-ray fluorescence spectrum. The classification of the piece corresponds to the reference spectrum determined to have the most similar spectral pattern.

In a further optional aspect, a conveyor conveys the piece of material through a detection area where the irradiating x-rays irradiate the piece and the fluoresced x-rays are detected from the piece, and an ejector corresponding to the classification of the piece having an input receives an ejection signal, and the ejector ejects the piece from the conveyor in accordance with the ejection signal at a point downstream from the detection area and associated with said classification.

In another optional aspect, the piece of material is flattened prior to irradiation and detection.

In still another optional aspect, the x-ray source is operative to generate the irradiating x-rays at a high intensity.

Optionally, but preferably, the x-ray source is an x-ray tube.

In another illustrative embodiment, a system for classifying a piece of material of unknown composition at high speeds is provided. The system includes means for irradiating the piece with x-rays from an x-ray source, causing the piece to fluoresce x-rays, means for detecting the fluoresced x-rays with an x-ray detector, and means for classifying the piece of material from the detected fluoresced x-rays.

In optional illustrative embodiments, the means for detecting and means for classifying are operative to detect the fluoresced x-rays and classify the piece, respectively, in a combined time of less than one second, less than 500 ms, less than 100 ms, less than 50 ms, and preferably even less than 15 ms.

Preferably, but optionally, the system includes means for determining an x-ray fluorescence spectrum of the piece of material from the detected fluoresced x-rays, and means for conditioning at least one of the irradiating x-rays and the fluoresced x-rays, respectively, such that speed and accuracy of determining the x-ray fluorescence spectrum is not significantly compromised or complicated by generation and detection of extraneous x-rays.

In yet another optional aspect, the means for conditioning includes means for filtering the irradiating x-rays to reduce a number of irradiating x-rays having an energy level too low to cause the piece to fluoresce x-rays having an energy level within a predefined range of the x-ray fluorescence spectrum.

In another optional aspect of the illustrated embodiments, the means for conditioning includes means for aiming the irradiating x-rays at the piece of material to reduce an amount of x-rays detected by the x-ray detector that were not fluoresced by the piece itself.

Preferably, but optionally, the means for aiming includes a collimator whose aperture components are made substantially of one or more materials that fluoresce at energy levels not within the predefined range.

For example, operative parts of the collimator may be formed essentially of polyvinyl chloride.

In another optional aspect, the means for conditioning includes means for aiming the x-ray detector at the piece of material to substantially confine the x-rays detected by the x-ray detector to those fluoresced by the piece and limit detection of other x-rays.

In another optional aspect, the x-ray fluorescence spectrum is determined for a predefined range of energy levels, and the means for aiming the x-ray detector includes a collimator whose aperture components are made of one or more materials that fluoresce at energy levels not within the predefined range.

For example, operative parts of the collimator may be formed essentially of polyvinyl chloride.

In yet another optional aspect, the system further includes means for conveying the piece of material through a detection area where the irradiating x-rays irradiate the piece and the fluoresced x-rays are detected from the piece, and the means for conveying includes a conveyor that may be formed essentially of one or more materials that fluoresce at energy levels not within the predefined energy range of the determined x-ray fluorescence spectrum so that the conveyor does not fluoresce x-rays that significantly interfere with determination of the x-ray fluorescence spectrum of the piece.

In an optional aspect, the conveyor is made essentially of polyvinyl chloride.

In still another optional aspect, the system further includes means for recognizing the spectral pattern of the determined x-ray fluorescence spectrum, and the means for classifying the piece base the classification on the recognition of the spectral pattern.

In another optional aspect, the means for detecting, means for determining, means for recognizing, and means for classifying are operative to detect the fluoresced x-rays, determine the x-ray fluorescence spectrum, recognize the spectral pattern of the x-ray fluorescence spectrum, and classify the piece, respectively, in a combined time of less than one second.

In a further optional aspect, the system further includes means for storing a plurality of x-ray fluorescence spectra as reference spectra on a computer-readable medium, each reference spectrum having a spectral pattern and corresponding to a different material classification, and the means for recognizing the detected spectral pattern includes means for comparing the determined x-ray fluorescence spectrum to each of the reference spectra to determine which reference spectrum has a spectral pattern most similar to the spectral pattern of the determined x-ray fluorescence spectrum, and the piece of material is classified as the material classification corresponding to the reference spectrum determined to have the most similar spectral pattern.

In yet another optional aspect, the system further includes means for flattening the piece of material prior to irradiation and detection.

In still another optional aspect, the system further includes means for irradiating the x-rays at a high intensity.

Optionally, but preferably, the x-ray source is an x-ray tube.

In another optional aspect, the system further includes means for conveying the piece of material through a detection area where the irradiating x-rays irradiate the piece and the fluoresced x-rays are detected from the piece, and means for actuating an ejector corresponding to the classification of the piece such that the piece is ejected from the conveying means at a point downstream from the detection area and associated with said clarification.

These and other features and advantages of the invention will be more readily understood and appreciated from the detailed description below, which should be read together with the accompanying drawing figures.

DETAILED DESCRIPTION

The combination of the high speed x-ray irradiation and detection techniques and the execution of a complex sorting algorithm described herein permit highly accurate classification and sorting of materials at very fast rates, at least one to two orders of magnitude faster than currently used techniques.

Figure 1:
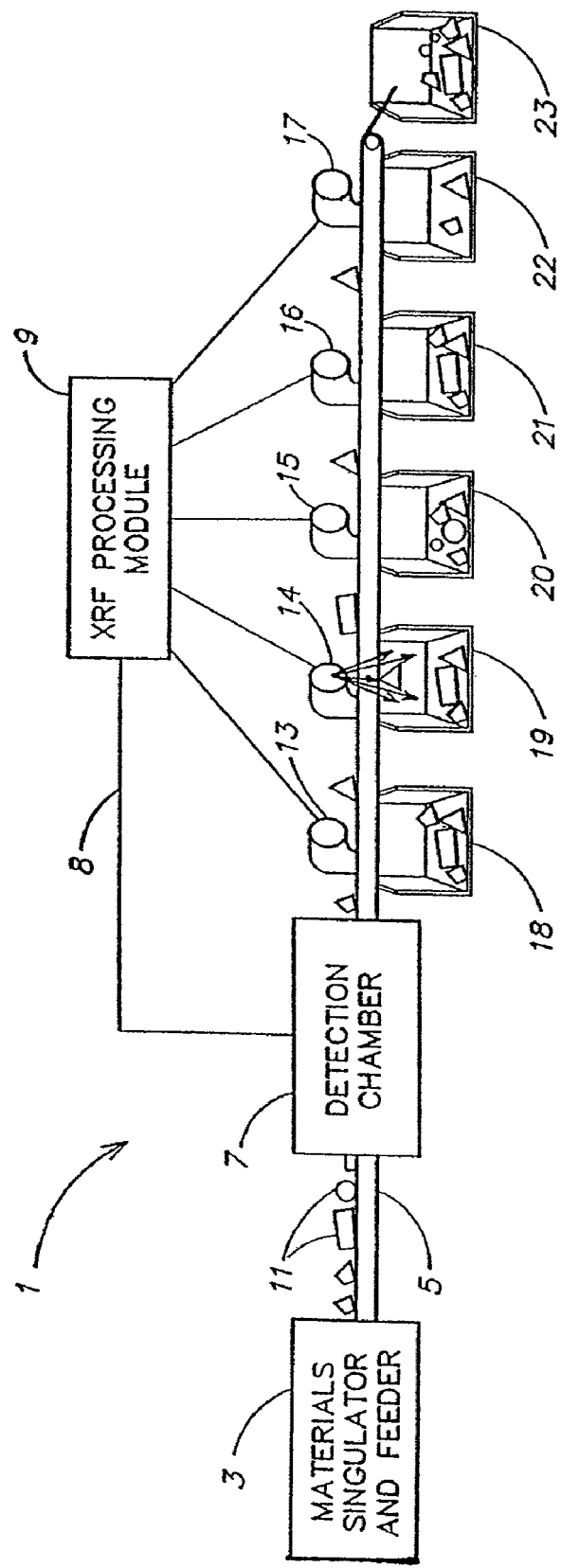
FIG. 1 is a diagram showing an illustrative embodiment of a high speed material sorting system.

FIG. 1 depicts an illustrative embodiment of a high speed material sorting system. A materials singulator and feeder 3 feeds a singulated stream of pieces of material 11 onto a conveyor belt 5. The conveyor belt 5 receives the pieces of material 11 and conveys the pieces through an x-ray detection chamber 7 downstream to be sorted into sorting bins 18-23. Although a conveyor belt is used in the illustrative embodiment of FIG. 1, any suitable conveying means may be used.

An x-ray detection chamber 7 receives each piece of material, irradiates the material with x-rays, and detects the x-ray fluorescence (xrf) from the materials as a result of the irradiation. The detection chamber 7 is also connected to an xrf processing module 9 through a signal carrier 8 such as, for example, a data bus. The xrf processing module 9 receives a signal representing the xrf detected from a piece of material along the signal carrier 8. The xrf processing module 9 then classifies the piece of material based on the xrf signature of the material, and activates a sorting device such as an air jet —for example, one of the air jets 13-17—that is mapped or assigned to the classification. When one of the air jets 13-17 receives a signal from the xrf processing module 9, that air jet emits a stream of air that causes a piece of material to be ejected from the conveyor belt 5 into a sorting bin corresponding to that air jet such as, for example, one of the sorting bins 18-22. High speed air valves from Mac Industries may be used, for example, to supply the jets with air pressure at, for example, 60-90 psi, with operating/closing times of 15 ms.

Although air jets are used to eject materials in the illustrative embodiment of FIG. 1, other methods may be used to eject the pieces of material, such as robotically removing the piece of material from belt 5, pushing the piece of material from belt 5, or causing an opening in the belt from which a piece of material may drop.

In addition to sorting bins 18-22, into which pieces of material are forced, the system 1 may also include a sorting bin 23 that receives pieces of material not forced from the belt 5. A piece of material may not be ejected from the belt 5 when the classification of the piece is not determined. Thus, sorting bin 23 may serve as a default bin into which unclassified pieces of materials are dumped. Alternatively, sorting bin 23 may be used to receive one or more classifications of pieces of material by deliberately not assigning any of the sorting bins 18-22 to the one or more classifications. This technique of default sorting can be particularly useful in sorting materials which fluoresce at low energy levels difficult to detect because of absorption by air such as, for example, aluminum.

Depending upon the classifications of materials desired, multiple classifications may be mapped to a single air jet and sorting bin. In other words, there need not be a one-to-one correlation between classifications and sorting bins. For example, it may be commercially beneficial to sort copper and brass into the same sorting bin. To accomplish this sort, when a piece of material is classified as either copper or brass, the same air jet may be activated to sort both copper and brass into the same sorting bin. The contents of this sorting bin may, for example, then be used to create a copper/brass alloy. Such combination sorting may be applied to produce any desired combination of material pieces and element distribution. The mapping of classifications may be programmed in the sorting application 35 of FIG. 4 to produce such desired combinations.

The classifications of pieces are user-definable and not limited to any known classification of materials. The classifications may be defined by using appropriate reference spectra, and programming the threshold values for these spectra, as is described in more detail below in connection with FIGS. 4 and 6. For example, the classification may be between: plastics, ceramics, glass, and, metals, such classification having a relatively broad scope; different metals and metal alloys such as, for example, zinc, copper, brass, chromeplate, and aluminum, such classification having a narrower scope; or between specific grades of steel, such classification having a relatively narrow scope. Thus, the classifications may be programmed to distinguish between materials of significantly different compositions such as, for example, plastics and metal alloys, or to distinguish between materials of almost identical composition such as, for example, different grades of steel.

Although FIG. 1 shows an illustrative embodiment of a high speed material sorting system in which the pieces of materials 11 are conveyed along a straight and level path, the system described herein is not limited to such an embodiment. In an alternative embodiment, the conveyor belt 5 may be divided into multiple belts in series such as, for example, two belts, where a first belt conveys the materials into the detection chamber 7, and a second belt conveys the pieces of material from the detection chamber 7. For example, the second belt may be at a lower height than the first belt, such that pieces of material 11 fall from the first belt onto the second belt through the detection chamber.

In an illustrative embodiment, an x-ray detector and x-ray source may be arranged such that the irradiation of x-rays onto or detected from the belt(s) is kept to a minimum (i.e., an acceptably low level), thus reducing detection of extraneous x-rays from the belt(s). (This both improves the speed and accuracy of classification as well as avoids "flooding" the detection needlessly.) In yet another embodiment, during conveyance through the detection area each piece of material may be slid across a window of material or air gap that allows x-rays to pass through, with the x-ray source situated to irradiate x-rays through the window.

In another illustrative embodiment, the part of the conveyer belt downstream from the detection chamber may be replaced by a circular conveyor, and the air jets 13-17, or other suitable removal means, arranged along the exterior or interior of the circular conveyor. In an optional aspect of this illustrative embodiment, the entire conveyor belt 5 is a circular conveyor, where the pieces of materials are fed onto the conveyer, and a detection chamber is located at a point along the conveyor.

In another illustrative embodiment of the high speed material sorting system, gravity may be used to accelerate the speed of the pieces of materials. For example, the conveying belt may convey pieces of material onto a surface that slopes downward leading toward the detection chamber 7. Further, at some point along the path of conveyance, the pieces of materials may be dropped into free fall, and be irradiated during free fall from an x-ray source or sources located along the sides. The fluoresced x-rays could also be detected during free fall from an x-ray detector or detectors located along the path of trajectory. Although such an arrangement reduces background radiation, the detection process becomes more complex. The location and speed of each falling piece must be detected to properly time the sorting process (constant speed cannot be assumed as in the previously discussed embodiments). Further, the inherent unstable nature of pieces rolling down a slope or in free fall introduces a variable element into the sorting process.

The system and process for classifying described herein may be applied to a handheld system for classifying pieces of material one at a time. In such a system, adjustments would have to be made for portability, but the general methods described herein for irradiating with x-rays, detecting fluoresced x-rays, building an xrf spectrum, and recognizing a spectral pattern of the xrf spectrum may be used.

Figure 2A:
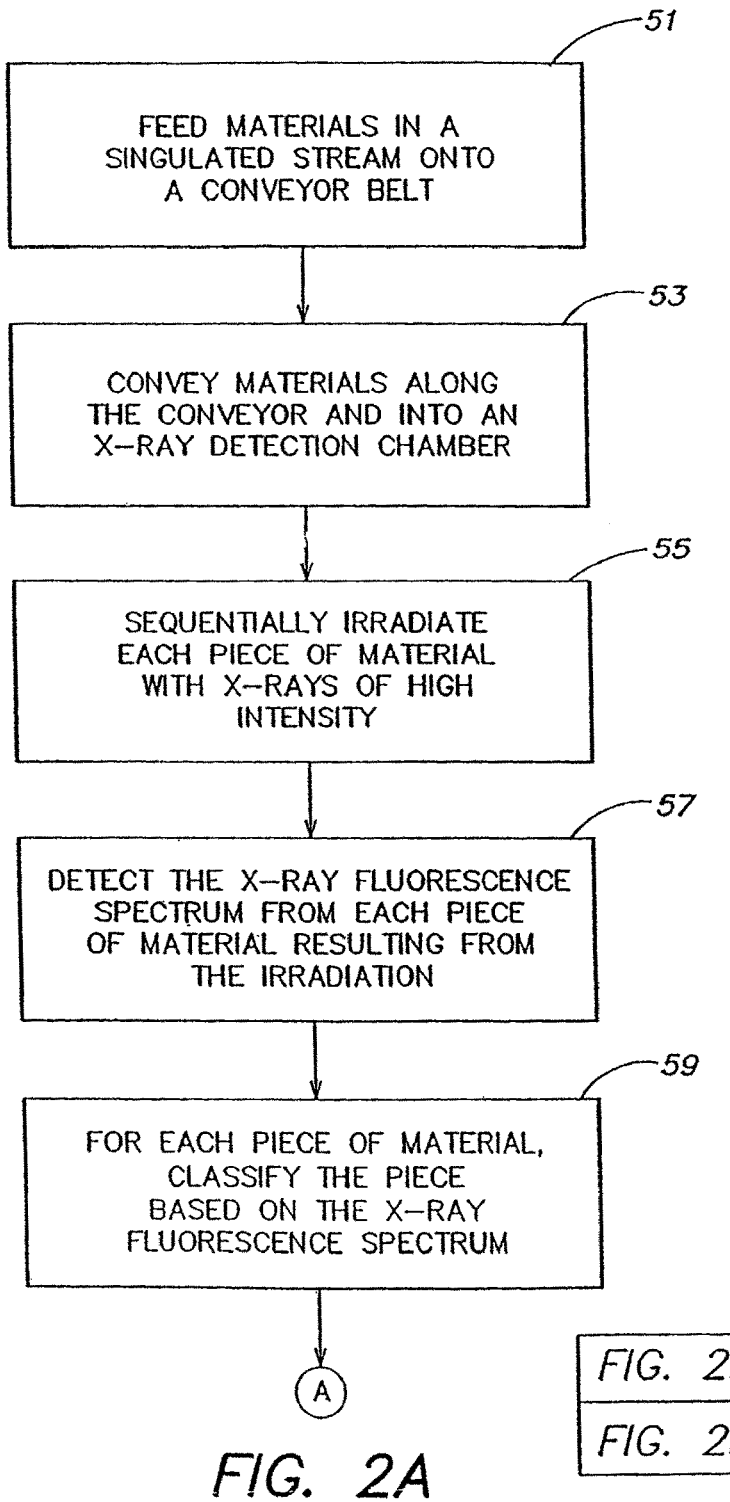
FIGS. 2A and 2B are a flow chart showing an illustrative embodiment of a process of sorting pieces of material at high speed.
Figure 2B:
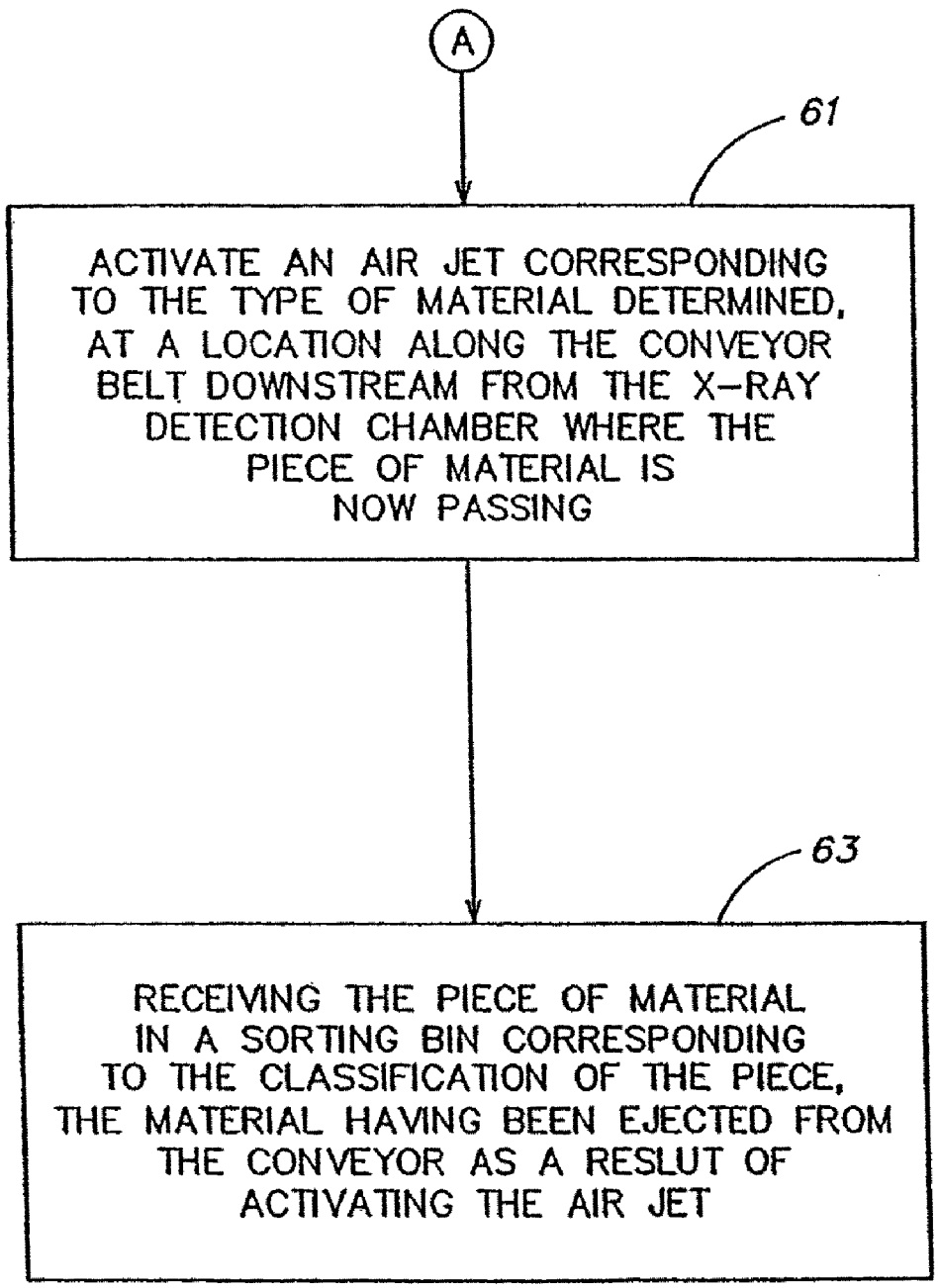

FIGS. 2A and 2B is a flow chart depicting an exemplary illustrative embodiment of a process of sorting materials at high speeds. First, in step 51, materials are fed in a singulated stream onto a conveyor belt. In an optional aspect of this illustrative embodiment, the materials are flattened with a flattening apparatus before being fed onto the conveyor belt 5. For example, a rolls crusher may be used for this purpose.

By flattening the piece of material, any other materials adhered to the piece of material may be removed. Further, flattening a piece of material before feeding the piece onto the conveyor belt improves sorting and classification of the materials. First, flattened pieces of material remain stationary on the conveyor belt, and do not roll. Thus, in the illustrative embodiment of FIG. 1, when a piece of material is classified, and an appropriate air jet 13-17 is actuated, the piece is in a position anticipated by the xrf processing module 9, and the piece is ejected from the conveyor belt into the appropriate sorting bin 18-22. Second, flattening the pieces of material provides a larger surface area to irradiate and from which to detect x-rays. Consequently, the piece of material is bombarded with and fluoresces more x-rays, resulting in a more complete xrf spectrum being determined for the piece of material. Third, the composition of the piece of material is less influenced by surface contaminants. Because during flattening, fresh material surfaces are exposed, a cleaner xrf spectrum is produced. Consequently, the spectra detected are more representative of the piece of material and not other materials that may be adhering to the surface of the piece of material.

In an illustrative embodiment, the conveyor belt 5 is depressed or troughed in the center such that pieces of materials gravitate to the center of the conveyor belt 5, where they remain more stationary and may be aligned directly beneath a detector.

Next, in step 53, the materials are conveyed along the conveyor belt and into an x-ray detection chamber. In an illustrative embodiment, each piece is flattened while being conveyed along the belt, as discussed above in connection with step 51.

Figure 4:
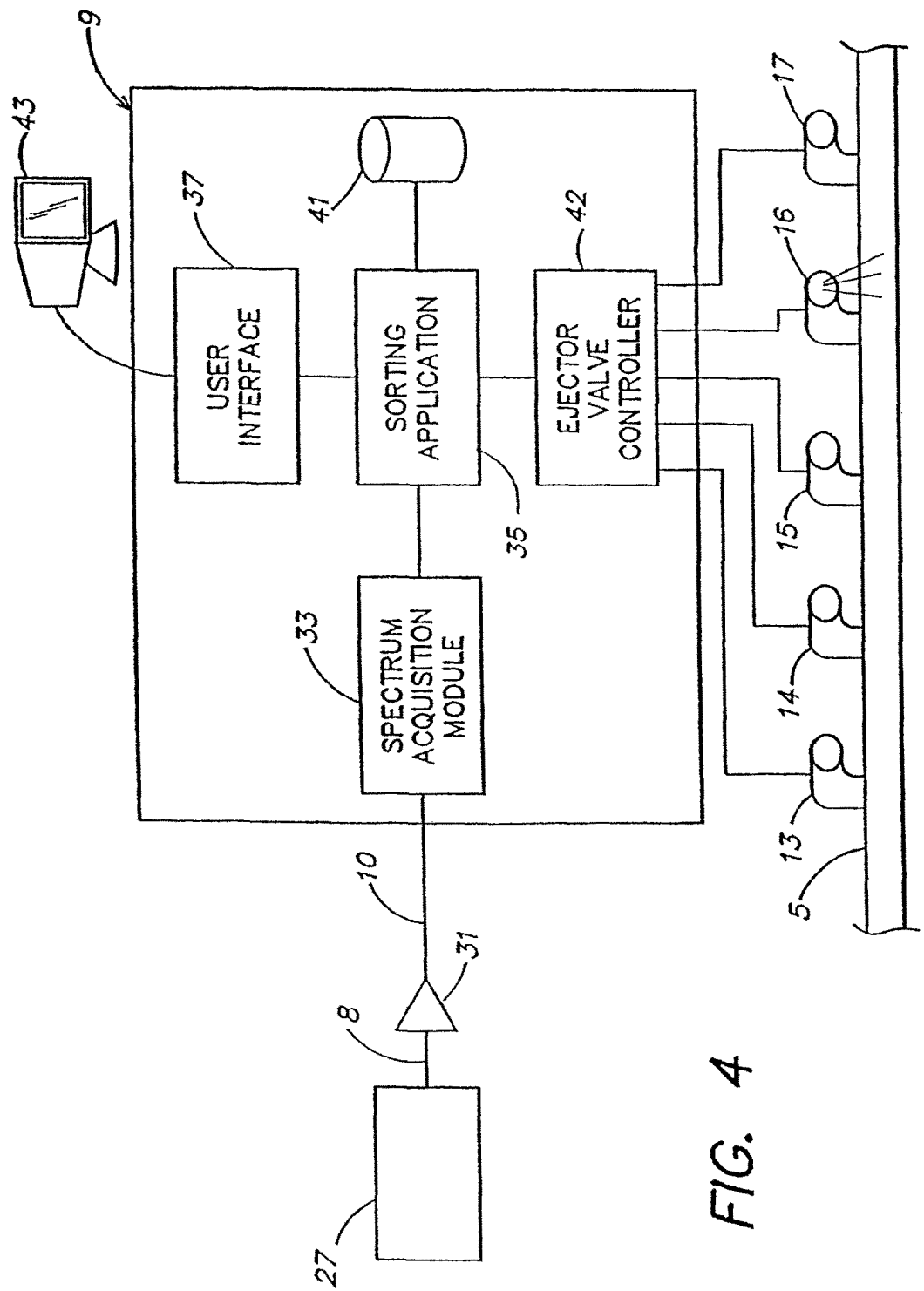
FIG. 4 is a block diagram showing an illustrative embodiment of an x-ray fluorescence processing module.

In an illustrative embodiment, the belt is comprised at least mostly of a material such as, for example, polyvinyl chloride (PVC), that when irradiated, fluoresce x-rays only at low energy levels, as will be disclosed in more detail with connection to FIG. 4. The speed at which the belt is operated is programmed in accordance with the spacing between the pieces of material and the cumulative time which it takes to: acquire or detect the x-rays from a piece of material; determine an xrf spectrum; and classify the piece. Such speeds may exceed 100 inches per second.

In step 55, when a piece of material has entered the x-ray detection chamber, the piece is irradiated with x-rays, as will be discussed below in more detail in connection to FIG. 4. The exposure to x-rays causes each material to fluoresce x-rays at various energy levels, producing an xrf spectrum. In step 57, this xrf spectrum is detected by an x-ray detector.

Next, in step 59, for each piece of material, the material is classified based on the xrf that was detected, as discussed in more detail below in connection to FIG. 3.

Next, in step 61 of FIG. 2B, an air jet corresponding to the classification of the piece is activated. Between the time at which the piece of material was irradiated and the time at which the air jet is activated, the piece of material has moved from the detection chamber to a point downstream from the detection chamber, at the rate of conveying of the belt. In an embodiment, the activation of the air jet is timed such that as the piece passes the air jet mapped to the classification of the piece, the air jet is activated and the piece of material is ejected from the conveyor belt.

In an alternative embodiment, the activation of air jet is timed by a respective position detector that detects when a piece of material is passing before the air jet and sends a signal to enable the activation of the jet. In step 63, the sorting bin corresponding to the air jet that was activated receives the ejected piece of material.

Figure 3:
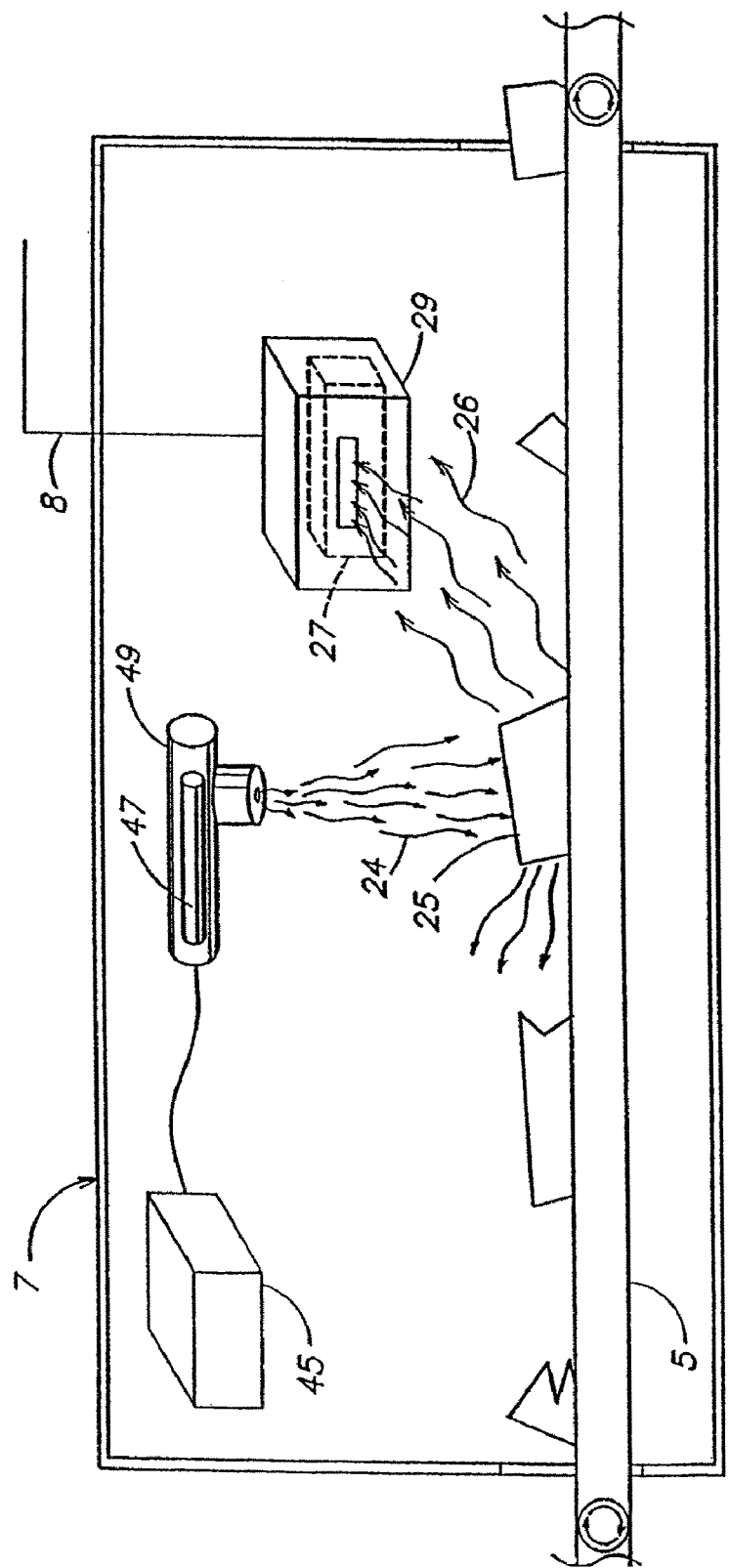
FIG. 3 is a diagram showing an illustrative embodiment of an x-ray detection chamber of a high speed material sorting system.

FIG. 3 is a diagram illustrating an illustrative embodiment of the x-ray detection chamber 7. A power supply 45 supplies power to an x-ray source 47. For example, the power supply may be a Spellman RMP 300 power supply, and the x-ray source 47 is an x-ray tube such as, for example, a water-cooled Varian OEG-50 x-ray tube. Such an x-ray tube and power supply combination is capable of operating at up to 300 watts at 30 kv. In an illustrative embodiment, the x-ray tube is operated at 13-17 kv at levels in the range of 1-10 watts.

The intensity of x-rays is proportional to the rate at which x-rays are transmitted. Although commercially available x-ray sources using radioactive isotopes, for example $Cd^{129}$, $Am^{241}$, and $Co^{57}$, and $Fe^{55}$ may be used as the x-ray source 47, as is common in material sorting systems that detect xrf, such isotope-based sources do not produce x-rays at the intensity that can be produced by an x-ray tube. The number of x-rays fluoresced 26 from a piece of material 25 irradiated with x-rays 24 is a function of the intensity and energy levels of the irradiating x-rays 24. Thus, when an x-ray source 47 is used that produces less intense x-rays 24, less x-rays 26 are fluoresced from the piece of material 25. Consequently, fluoresced x-rays 26 must be detected from the piece of material 25 for a longer period of time so that an xrf spectrum with a strong enough image, i.e. a recognizable spectral pattern, may be determined.

Therefore, to increase the speed of detection and classification, an x-ray tube may be used as the x-ray source 47. An x-ray tube is capable of producing x-rays several orders of magnitude more intense than any commercially available isotope-based x-ray sources. This intensity is particularly important when the piece of material 25 is relatively small, when the x-ray source 47 is a relatively long distance away from the piece of material 25, or when the piece of material 25 is a relatively long distance away from the detector 27, the reasons for which are discussed in more detail below. Further, an x-ray tube has the added advantage of being capable of being turned off when not in use, in contrast to a radioactive isotope. As used herein, the term "high intensity" when used to describe x-rays means x-rays of an intensity at least an order of magnitude more intense than the x-rays produced from a typical, commercially-available isotope-based x-ray source.

Using an x-ray tube, or another comparable high intensity radiation source, as the x-ray source 47, however, causes massive amounts of x-rays to be present in the x-ray chamber 7, orders of magnitude more than would be present if an isotope-based source were used. The presence of this amount of x-rays causes problems with the detection of x-rays by the x-ray detector 27 and the determination of an accurate xrf spectrum. Therefore, the irradiation and detection of the x-rays must be conditioned as described in more detail below.

In an illustrative embodiment, the x-ray source 47 is collimated by a collimator 49, having an aperture which is aimed at a detection area where a particular piece of material 25 is to be irradiated. In an illustrative embodiment, the detection area is approximately a circle with a diameter of about 2.5". As used herein, a "collimator" is a device having an aperture which limits the transmission of x-rays of an x-ray stream such that the x-rays move in the same, or nearly the same, direction.

An x-ray detector 27 detects the x-rays fluoresced from the piece of material 25, and sends a signal representing the detected x-rays along the signal carrier 8 to the xrf processing module 9. In an illustrative embodiment, the x-ray detector 27 is collimated by a collimator 29. An aperture of collimator 29 aims x-ray detector 27 at the piece of material 25 during detection such that detector 27 directly receives fluoresced x-rays 26 from piece of material 25 while extraneous x-rays including x-rays 24 irradiated from x-ray source 47 and incidental x-rays from other objects within the detection chamber 7 are inhibited by collimator 29 from reaching detector 27, thereby reducing detection of these extraneous x-rays by detector 27. These direct and incidental x-rays are referred to herein as background noise. Background noise includes x-rays fluoresced or reflected from objects in the chamber 7 other than the piece of material 25, including: the interior surfaces of the chamber 7 itself; items used to fasten together sections of the chamber 7 itself; the conveyor belt 5; or any other objects present in the chamber. Such background noise may be caused by the irradiating x-rays 24 and fluoresced x-rays 26 impacting other objects in the chamber 27 and causing secondary fluorescence.

In an illustrative embodiment in which a high intensity x-ray source 47 is used, the high intensity x-rays 24 bombarding the piece of material 25 cause the piece of material 25 to fluoresce x-rays 26 of high intensity. Because of these high intensity x-rays, it is necessary to use an x-ray detector 27 capable of handling the high intensity xrf without flooding. An example of an x-ray detector capable of handling the high intensity fluorescence x-rays is the Amptek XR-100T with Si-PIN diode detector and beryllium window to admit low energy x-rays. The energy resolution of the Amptek detector is 250 ev or 0.25 Kev. However, improved x-ray detectors are currently being developed which are capable of even smaller (more precise) energy resolution. Thus, the choice of resolution of an xrf spectrum is a function of the resolution desired and the resolution capability of the x-ray detector 27.

In an illustrative embodiment, the x-ray detector 27 is highly sensitive, and when too many x-rays impact the x-ray detector 27, it may become flooded with fluoresced x-rays. Such flooding may cause the x-ray detector 27 to malfunction or reduce the accuracy of the determined xrf spectrum. When too many x-rays impact the x-ray detector 27, the accuracy of the spectrum determination may be reduced because not all of the fluoresced x-rays 26 will be detected. Thus, in an illustrative embodiment, accurate classification is best achieved by generating x-rays 24 at an intensity that will not cause the x-ray detector 27 to be flooded by irradiation. Thus, the x-ray 47 source may be operated at power levels to produce relatively low intensity radiation such as, for example, at 13.5 V and 0.03 mA, giving an x-ray power output of only 0.4 watts.

The x-rays 24 emitted by the x-ray source 47 may be filtered by an x-ray filter. Such filtering is beneficial when an x-ray source 47 that has a broadband energy output (emits x-rays of a wide range of energy levels) for example, an x-ray tube, is used. Such broadband energy includes unneeded x-rays that produce increased background noise in the x-ray detection chamber 7. Unneeded irradiated x-rays are irradiated x-rays of an energy level insufficient to cause the piece of material 25 to fluoresce x-rays within an energy range of the determined xrf spectrum. For example, if the determined x-ray spectrum is programmed to have an energy range between 5 kev and 30 kev, then only fluoresced x-rays 26 within this range are relevant for classification of the piece 25. Generally, to cause the fluorescence of an x-ray at a given energy level, an impacting irradiated x-ray must have an energy level equal to or greater than the given energy level. Thus, to cause the fluorescence of an x-ray of between 5 kev and 30 kev, an impacting irradiated x-ray must have an energy level of at least 5 kev. Thus, any x-rays irradiated 24 from the x-ray source 47 that are less than approximately 5 kev are unneeded. The term extraneous x-rays, as used herein, includes both background noise and unneeded irradiated x-rays. The unneeded x-rays may cause additional background noise, and the unneeded x-rays alone or in combination with the background noise may flood the x-ray detector 27. Thus, an x-ray filter may be used to reduce the number of unneeded x-rays impacting the piece of material 25 or impacting the x-ray detector 27.

As discussed above, in an illustrative embodiment using a high energy x-ray source, such as an x-ray tube, a high amount of background noise is generated. Although typically a conveyor belt made of some sort of rubber material is used in sorting systems, the intensity of the x-rays 24 generated from the x-ray source 47 cause even elements present in a rubber belt to emit x-rays. Therefore, in an illustrative embodiment, the belt preferably is made of a material that will not fluoresce x-rays at energy levels that fall within the range of the energy spectrum being detected, thereby interfering with the energy spectrum. The energy level of the fluoresced x-rays depends on the energy levels at which the elements present in the piece of material 25 fluoresce. The energy level at which an element fluoresces is proportional to its atomic number. For example, elements of low atomic numbers fluoresce x-rays at lower energy levels. Thus, the material for the conveyor belt may be chosen such that the belt comprises elements of certain atomic numbers that do not fluoresce x-rays within a certain energy range. For example, PVC contains chloride which fluoresces at a low energy level, and therefore, when an xrf spectrum with a relatively high energy range is being determined, PVC may be a good choice as a material for the conveyor belt.

For the same reasons as discussed above with respect to the conveyor belt 5, the x-ray detection chamber 7, or at least the interior surface of the x-ray detection chamber 7, may be made or lined with a material that fluoresces at particular energy levels such as, for example, PVC. Further, the collimator 49 for the x-ray source 47 may be made of a material that fluoresces at particular energy levels such as, for example, PVC.

X-ray chambers, such as x-ray chamber 7, are typically shielded with a layer of lead along the interior surface to absorb the x-rays and thus protect persons in the vicinity of the x-ray chamber. In a high speed material sorter, however, when a high intensity x-ray source such as an x-ray tube is used, if the intensity is high enough, the lead itself begins to fluoresce x-rays at a level that may interfere with the detector. If there are enough x-rays fluoresced from the lead, the x-ray detector may be flooded, and the accuracy of the determined xrf spectrum may be reduced. To reduce the probability of flooding the x-ray detector 27, the x-ray chamber 7 may be lined with a material, for example, PVC, that fluoresces x-rays at lower energy levels at which the x-rays have a higher probability of being absorbed by air.

Besides reducing the accuracy of the xrf spectrum by flooding, the xrf spectrum may be further compromised by incorrectly indicating that the piece of material 25 contains lead, or a different amount of lead than is correct, which may lead to incorrect classification. Such a situation would arise if lead fluoresced within the energy spectrum being determined. In such a situation, to avoid loss of x-ray fluorescence spectrum accuracy, lead should not be used to line the interior surface of the x-ray chamber.

In an illustrative embodiment, the xrf detected by the x-ray detector 27 is collimated by a collimator 29. The collimator 29 limits the effects of extraneous x-rays being received by the x-ray detector 27, by aiming the detector 27 at the detection area where the x-rays 26 are fluoresced by the piece of material 25. In an illustrative embodiment, this collimator 29 is made of a material or materials that fluoresces at particular energy levels such as, for example, PVC, for the same reasons discussed above with respect to collimator 49, x-ray chamber 7, and conveyor belt 5.

Thus, when using an x-ray source 27 of high intensity, such as an x-ray tube, the irradiation and detection of the x-rays may be conditioned in order to accurately detect the xrf of a piece of material and accurately classify the piece. Conditioning the irradiated x-rays may include collimating the x-ray source 49 and filtering the x-rays 24 produced by the x-ray source 47. Conditioning the detection of x-rays may include collimating the x-ray detector 27, and using materials that fluoresce at low energy levels for many of the components proximate to detection area such as, for example, the conveyor belt 5 and the x-ray chamber 7.

For high speed sorting of materials using an x-ray source that produces x-rays of high intensity, collection intervals for collecting x-ray spectra may range lower than 10 ms (ms). Longer intervals such as, for example, 5 seconds, may be used to collect reference spectra that are stored for comparison against detected spectra. Generally, the long-time spectra are less noisy than the shorter duration samples since random variations of the fluorescing and detection of x-rays thus of the output of the detector 27, tend to cancel over time.

In the illustrative embodiment of FIG. 3, the x-ray source 47 is located above the detection area. In alternative illustrative embodiments, the x-ray source may be located to the side of detection area, or beneath the belt. Locating the x-ray source beneath the detection area, however, requires maintaining a surface, perhaps a portion of the belt, through which the x-rays must penetrate to irradiate the piece of material 25. In such an illustrative embodiment, the belt may have a mesh configuration, or may have apertures through which x-rays may pass through the belt impeded mainly by the x-ray absorption of air. Further, the composition of the belt may be such that the belt is largely transparent to the transmission of x-rays. Although locating the x-ray source beneath the detection area requires maintaining a surface, such an arrangement does place the x-ray detector closer to materials, regardless of the size of the materials. This arrangement therefore may increase the number of irradiating x-rays that impact the piece of materials, resulting in an increased number of x-rays fluoresced and an increased number of detected x-rays.

FIG. 4 is a diagram illustrating an illustrative embodiment of the xrf processing module 9. The x-ray detector 27 sends a signal that carries the xrf detected from the piece of material 25 along a signal carrier 8. The xrf signal is amplified by amplifier 31 to produce an amplified xrf signal transmitted on signal carrier 10 which is received by a spectrum acquisition module 33. In an illustrative embodiment, the amplifier 31 is an A250 preamplifier that conditions the signal to produce the amplified xrf signal on signal carrier 10.

Figure 5:
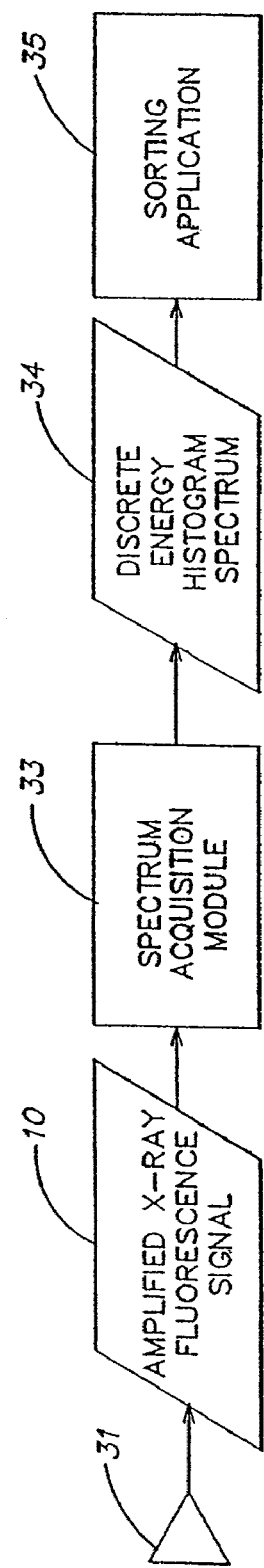
FIG. 5 is a data flow diagram showing an illustrative embodiment of the function of a spectrum acquisition module.

FIG. 5 is a data flow diagram illustrating an illustrative embodiment of the function of the spectrum acquisition module 33. The spectrum acquisition module 33 receives the amplified xrf signal and converts the amplified xrf signal into a discrete energy histogram spectrum 34. In an illustrative embodiment, the spectrum acquisition module comprises an Amptech MCA 5000 acquisition card and software programmed to operate the card at a real-time rate. The Amptech MCA card has 2048 channels for dispersing x-rays into a discrete energy spectrum with 2048 energy levels. In this illustrative embodiment, for each collection interval, the energy count for each energy level may be stored in a separate collection register. A processor of the xrf processing module 9 may then read each collection register to determine the number of counts for each energy level during the collection interval, and build the energy histogram. The processor interfaces to the Amptech card by executing I/O reads and writes across a bus such as, for example, an ISA bus. In this illustrative embodiment, the general procedure for obtaining a spectrum is: load timer registers, issue start collection command, wait for done status, and copy the collection registers to a computer-readable memory.

Figure 6:
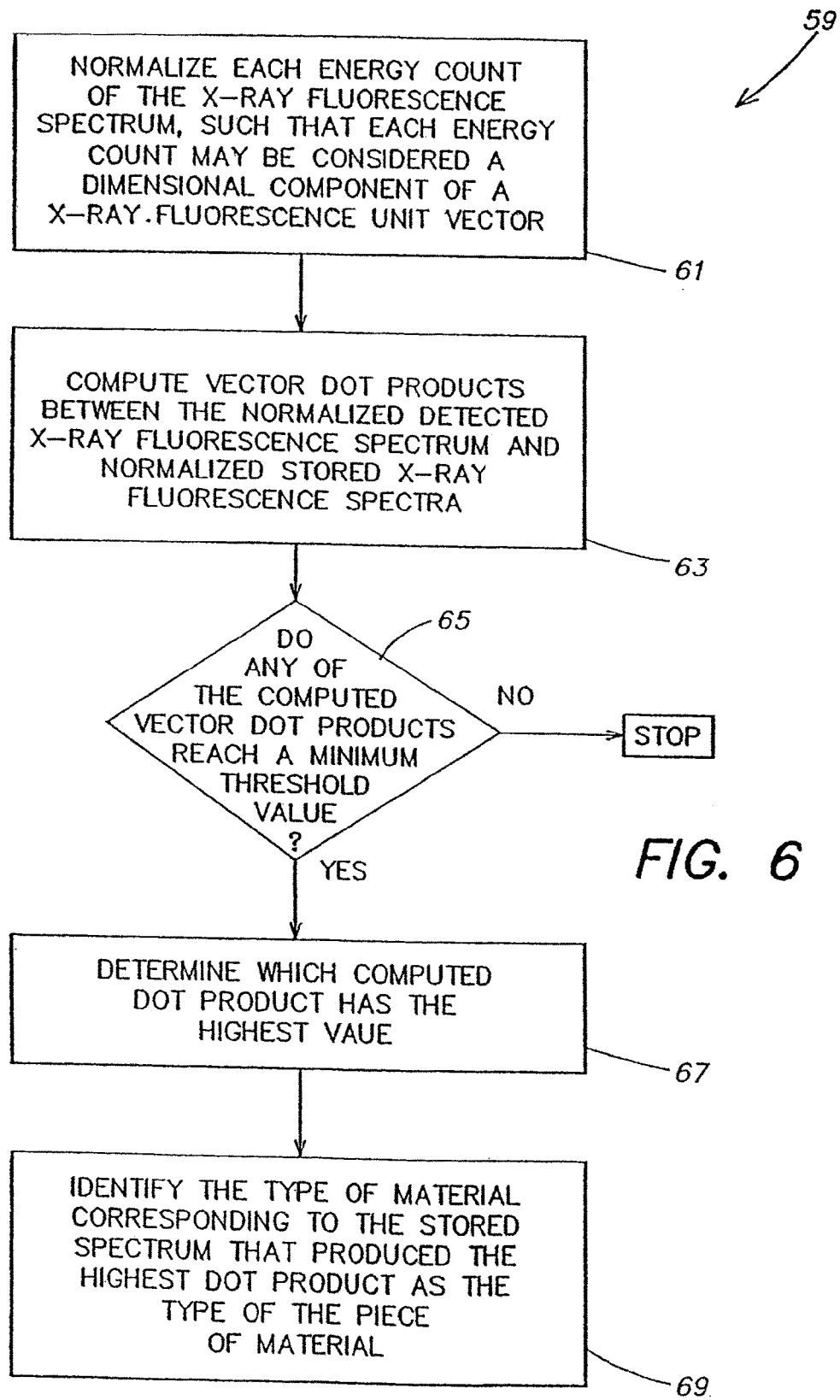
FIG. 6 is a flow chart showing an illustrative embodiment of a process for classifying a piece of material based on the x-ray fluorescence spectrum of the piece.

The sorting application 35, also referred to herein as the classification module, executes a sorting algorithm that classifies the piece of material 25 by recognizing the spectral pattern of the xrf spectrum of the piece. FIG. 6 is a flow chart showing an illustrative embodiment of step 59 of FIG. 2A for classifying the piece based on the xrf spectrum of the material. In step 59, each energy count of the xrf spectrum is normalized such that each energy count may be considered a dimensional component of an xrf unit vector. Accordingly, each energy count is reduced by an amount equal to:

$$\frac{1}{\sqrt{(a^2 + b^2 + c^2 \ldots n^2)}}$$

where a, b, c and n are energy counts at various energy levels.

The energy range of the xrf spectrum determined by the spectrum acquisition module 33, the number of energy levels of the determined xrf spectrum, and the resolution of the determined xrf spectrum are all programmable. These parameters may be chosen depending on the sort to be performed. If a large range of materials are being sorted, the energy range may be large and the number of energy levels high. If pieces of materials are to be sorted have relatively similar compositions, then the resolution may be fine, so as to distinguish between the spectral patterns. For example, when pieces of metal are to be sorted into aluminum, brass, chrome plated zinc, copper, stainless steel, and zinc, the spectrum acquisition module 33 may be programmed to detect and count x-rays at 256 energy levels ranging from 0 kev to 25.6 kev with 0.1 kev resolution.

Next, in step 63, the vector dot products are computed between the normalized detected xrf spectrum and the normalized xrf spectra of any stored reference materials. Prior to starting the sorting process, a set of reference samples is collected and the xrf spectra of these samples determined and stored, for example, in a non-volatile storage medium 41. In an illustrative embodiment, for reference spectra, the x-ray spectrum of each reference material is collected over an interval of 5 seconds.

To compute the dot product, if the detected normalized reference spectra has normalized energy counts of $a_1, a_2, \ldots a_{256}$, and the normalized xrf spectrum of a reference material has normalized energy counts of $b_1, b_2, \ldots b_{256}$, then the vector dot product between these two spectra would be $a_1 \times b_1 + a_2 \times b_2 + \ldots a_{256} \times b_{256}$. Because all the spectra have been normalized to a unit vector, the dot products between two identical spectra would produce the value 1, where the results of all dot products should be between the 1 and 0. A dot product of 0 results if for every energy level of the detected spectrum for which at least a single count is detected, the reference spectrum does not have a single energy count, or vice versa.

A user interface 37 provides functions to sample, view, and compare individual spectrums to prepare the reference material set and to designate which references will be "active" and read into faster volatile memory for use during execution of the sorting algorithm. Thus, the xrf processing module computes a vector dot product between the normalized xrf of the detected material and the normalized xrf spectrum of each of the active reference materials.

Next, in step 65, it is determined whether any of the computed vector dot products reach a minimum threshold value. In an illustrative embodiment, there is a single minimum threshold value that must be achieved for any of the reference spectra. In an alternative illustrative embodiment, each reference spectrum has an individual minimum threshold value that the dot product calculated for the reference spectrum must equal or exceed. Having an individual threshold value for each reference spectrum adds additional flexibility in distinguishing between similar spectral patterns, as is discussed in more detail below.

The threshold values for reference spectra are programmable by a system user. The closer the spectral patterns of two reference spectra, the higher the threshold value for these reference spectra should be programmed in order to positively distinguish the two spectra. For example, if a user is only interested in distinguishing between a first spectral pattern that has several peaks at certain energy levels, and a second spectral pattern that has energy peaks at certain other energy levels, then the user may program the threshold value for these two reference spectra to be relatively low to distinguish between the two spectral patterns (although the threshold value should be high enough to distinguish the two reference spectra from other reference spectra). Conversely, if two spectral patterns have energy peaks that share common energy levels and where, for these energy levels, the normalized count value for each spectra is close to the other, then the threshold value should be set relatively high. The value of the threshold must be set high enough so that the spectral pattern of a detected piece of material must be very close to matching one of the two reference spectra for a classification to be made. This high threshold ensures correct recognition of a spectral pattern.

If it is determined in step 65 that at least one vector dot product reaches a minimum threshold value, then at step 67 it is determined which computer dot product value has the highest value. The dot product of the highest value indicates the reference spectra closest to the detected spectra. In an alternative illustrative embodiment, where each spectrum has an individual threshold value, it is determined for which of the reference spectra the highest dot product was calculated for which the minimum threshold for the reference material was reached.

Consequently, in step 69, the classification corresponding to the stored spectrum that produced the highest dot product and equals or exceeds a minimum threshold is determined. Such a classification may be encoded on a classification signal. In an alternative illustrative embodiment of step 69, the classification corresponding to the stored spectrum whose dot product exceeds the spectrum's threshold value by the greatest percentage is selected. For example, assume spectra A has a threshold of 0.4 and spectra B has a threshold of 0.6. In addition, assume a dot product of 0.7 is calculated for spectra A and a dot product of 0.8 is calculated for spectra B. The classification corresponding to Spectra A would be selected even though Spectra B's dot product is higher because Spectra A's dot product is 75% over its threshold, while Spectra B's dot product is only 33% over its threshold.

Classifying a piece of material by comparing the spectral shape or spectral pattern of the xrf of a spectrum contrasts to known methods of analyzing only energy counts of select peak energy levels. Such known methods merely determine whether the number of counts for select energy level exceeds a threshold value, or compare the counts of the select energy levels to the counts from corresponding select peak energy levels of a reference spectrum. Each selected energy level is typically indicative of a particular element present in the piece of material. In some known systems, the selected peaks are normalized, such that the resulting normalized peaks reflect the proportion of each element in the piece of material. Typically, known methods require that the xrf of a piece of material is detected over a relatively long period of time such as, for example, a second or more. Detecting over such a long period ensures that the selected peaks accurately reflect the proportion of each element.

The sorting algorithm described herein is a faster and more flexible method of classifying a piece of material than those known methods described above. First, comparing the spectral pattern or image of the detected xrf spectrum to the spectral pattern or image of stored reference spectra permits an accurate classification to be made even when only a faint or weak image of the xrf spectrum of a piece of material is known (i.e. the detected spectral pattern takes the general shape of the spectral pattern of a reference spectrum). Therefore, precise composition of a piece of material need not actually be determined (although it may be). Such a faint image results when a relatively limited number of x-rays or counts have been detected. Less counts result from shorter detection times. Thus, recognition of a faint image permits a piece of material to be classified in shorter detection times, substantially less than one second, possibly shorter than 10 ms.

Second, the sorting algorithm described herein permits a material sorting system to have greater flexibility in sorting materials than do known sorting algorithms allow. A user may select a random sample to use as a reference sample, establish the random sample as a reference spectra by detecting the xrf from the random sample for a relatively long interval of time, for example 5 seconds, in order to eliminate any random variations in the detected xrf, and store the xrf spectrum determined from the detected x-rays. The xrf spectrum of the random sample can then serve as a reference spectra by which other pieces of material can be detected and compared against to determine whether the determined xrf spectra matches the reference spectra created from the random sample. A user would not have to program the processing module to analyze certain peak energy levels of the new reference xrf spectrum and future determined xrf spectra. In contrast, the sorting algorithm would compare the spectral patterns without regard for peak energy levels. Known sorting methods require that sorting parameters be reconfigured to analyze the peak energy levels of the reference xrf spectra and determined xrf spectra.

Figure 7A:
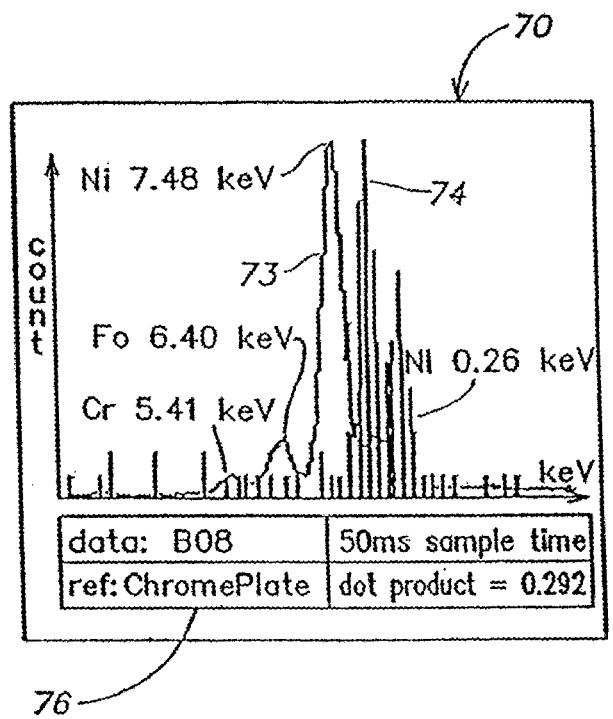
FIG. 7A is a diagram showing an illustrative embodiment of using an energy histogram to represent an x-ray fluorescence spectrum.
Figure 7B:
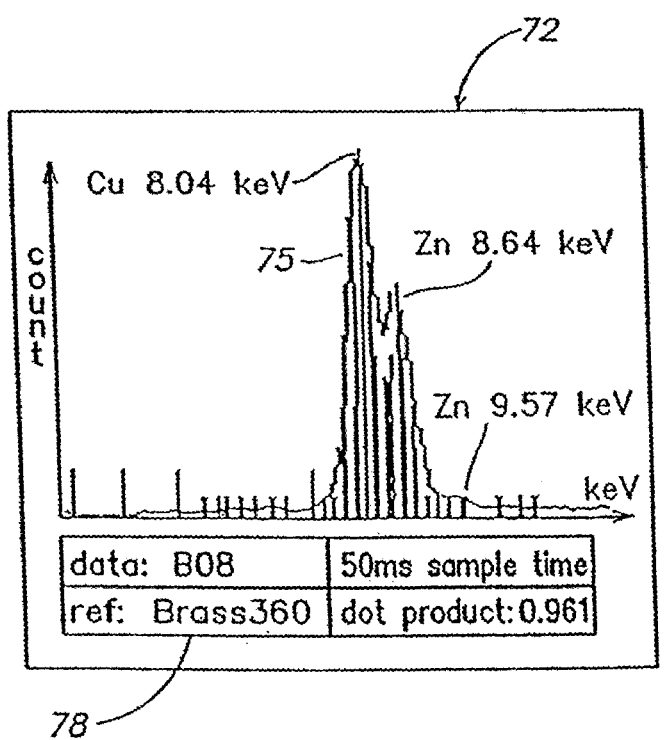
FIG. 7B is a diagram showing an illustrative embodiment of using an energy histogram to represent an x-ray fluorescence spectrum.

FIGS. 7A and 7B are each a diagram illustrating an illustrative embodiment of using energy histograms to represent an x-ray fluorescence spectrum. Energy histogram 70 represents the comparison between the xrf spectral pattern of an unknown piece of material B08 and the xrf spectral pattern of chromeplate. Energy histogram 72 represents the comparison between the xrf spectrum of B08 and the xrf spectrum of brass 360. For illustrative purposes, the xrf spectral pattern of B08 is represented as a discrete energy counts, while the xrf spectral patterns of reference materials chromeplate and brass 360 are represented as a curve. For example, in energy histogram 70, 74 represents a discrete energy count of B08.

The reference spectral curves 73 and 75 illustrate the fact these spectral patterns were constructed from xrf collected over a significantly longer collection interval than the detected pattern. Thus, the reference curves 73 and 75 are a more complete image of their respective xrf spectra than the faint image presented by the energy counts of B08.

The energy histograms 70 and 72 indicate that the unknown material B08 is a piece of brass, the xrf of which was collected over a relatively brief interval of time such as, for example, 50 ms. The reference materials chromeplate and brass 360, on the other hand, are collected over a relatively long period of time, for example 5 seconds. As can be seen from the energy count histogram 72, from the energy histogram itself and from the information panel 78, the brass reference, brass 360, is a very close match to the brass sample B08. The lower right box of the information panel 78 indicates that the vector dot product produced from the comparison of these two spectral patterns is 0.961. On the other hand, as shown by energy histogram 70, the chrome plate reference is not a very close match for the brass sample B08. This is indicated visually in the energy count histogram itself and also by the vector dot product of 0.292 indicated in the lower right hand box of the information panel 76.

In FIGS. 7A and 7B, energy peaks of various elements present in the materials are identified. For example, nickel (Ni) has an energy peak at 7.48 keV. As discussed above, known systems are typically limited to analyzing only the energy peaks, such as those shown in the energy histograms of FIGS. 7A and 7B. These energy peaks are highly indicative, however, of the composition of the reference material or the sample material. The partial dot product calculated between two energy peaks, comprising the multiplication of the normalized energy counts from each spectra at these energy peaks, has a greater impact on the overall vector dot product than the partial dot products produced by multiplying lower energy counts. Thus, the sorting algorithm described herein, although considering a large range of energy levels, still statistically gives more weight to the peak energy levels characteristic of the elemental materials included in a material.

Returning to FIG. 4, the sorting application 35 accesses spectral data from the spectrum acquisition module 33 and uses the data to execute the sorting algorithm described above to determine which of the air jets 13-17 to activate in accordance with the classification of the piece of material. The sorting application 35 may also store data in a non-volatile computer readable medium 41 such as, for example, a database. The database may be implemented with Microsoft Access, Cybase, Oracle, or other suitable commercial database systems. Such data may include xrf spectra received from the spectrum acquisition module 33, sorting parameters, and the results of comparisons, e.g., dot products, between detected xrf spectra and reference xrf spectra. Once the data is stored in a database, such data may be analyzed using known database analysis tools, such as a query language such as, for example, Microsoft SQL.

The sorting application 35 also sends data to and receives commands from a user interface 37 that may provide a visual display to a system user on a video display device such as a monitor 43. The details of the graphical display produced by the user interface 37 is described in more detail below in connection with FIG. 8.

In an illustrative embodiment, the sorting application 35 executes at a real time rate, the functionality required by the sorting algorithm executed by the sorting application 35 being separate from the user interface 37. In an illustrative embodiment, the xrf processing module 9 runs an operating system on a computer such as, for example, WindowsNT®, a general-purpose operating system. Other known commercial operating systems suitable to implement the sorting application 35 and the user interface 37 may be used. In an illustrative embodiment, the delays in timing uncertainties introduced by WindowsNT affect only the user interface and not the sorting algorithm.

In an illustrative embodiment, all software system components are written for WindowsNT 4.0 using Microsoft Visual C++ and Imagination Systems' HyperKernel real-time extension. The Sommer application discloses source code that may be used to implement the sorting application 35.

In an illustrative embodiment, the sorting application 35 executes on a real-time operating system.

In an alternative illustrative embodiment, the sorting application 35 is a real-time module that executes "underneath" the operating system, and contains the entire sorting algorithm as well as any necessary sorting-hardware references. A real-time extension such as, for example, the Imagination System's HyperKernel, of the Windows NT operating system may provide guaranteed real-time control that is isolated from the non-deterministic delays introduced by a general-purpose task scheduler. HyperKernel library functions may be used for unrestricted access to an ejector air valve controller 42, and to registers of external hardware, such as a hardware illustrative embodiment of the spectrum acquisition module 33.

The sorting algorithm described herein requires that spectra be captured and processed at a precise rate with millisecond accuracy. The speed and precision of this execution are functions of the actual time for executing the algorithm code, and the scheduling of the timed events in a multi-tasking environment. If the time required to execute the algorithm were to exceed an inter sample period, then an auxiliary embedded processor would be required. If a host computer has sufficient bandwidth to execute the algorithm within the required time, the operating system must also ensure that the algorithm's tasks are not delayed by tasks from other application or system service processes.

The second requirement is often the most difficult to satisfy. Although, contemporary PC hardware provides sufficient processing power to execute all but the highest data-rate or most calculation-intensive algorithms, general purpose multi-tasking operating systems, like Windows NT, cannot guarantee real-time millisecond-precision service for the algorithm's code. In an illustrative embodiment, a separate embedded processor board is used to guarantee real-time execution of the sorting algorithm, even when the host CPU may have adequate bandwidth. In another illustrative embodiment, a real-time extension to WindowsNT is implemented to provide guaranteed time-slices to the sorting algorithm. The real-time extension allows the algorithm to be implemented as a multi-threaded application system with guaranteed sub-millisecond real-time precision, so that the operating system (and its extension) scheduler satisfies the second requirement. The result is a xrf processing module 9 that can support the sorting algorithm without the cost of an additional embedded processor board.

The sorting algorithm executed by the sorting application 35 requires that xrf be detected, the spectral pattern determined, and the piece be of material be classified over short time intervals such as, for example, less than a second. The processing speed of most of today's commercial PCs permits execution of the sorting algorithm in less than 1 ms. Even a computer system implementing a 166 megahertz Pentium processor can execute the sorting algorithm in less than 2 ms if run as a single non-interrupted thread of execution. The x-ray detector 27, however, requires 10 ms to 50 ms to acquire the spectrum, depending on the intensity of the x-ray source 47, the respective distances between the x-ray detector 27, the x-ray source 47, and the piece of material 25 during detection, the composition of objects within the x-ray chamber, the conditioning of the x-ray detection and irradiation, the duration of the detection, and various parameters of the x-ray detector 27. Thus, the speed of the entire process is essentially limited by the acquisition time for the spectra.

The amount of xrf detected from a piece of material depends on the detection time, which depends on the size of the piece of material and the time the material spends in the detection area. Systems that rely on the number of energy counts, as opposed to the proportional relationship between energy counts must know the size of the piece of material and the time spent under the x-ray detection device by the material. The high speed material sorting system and process described herein may be used to sort materials of various sizes because the sorting algorithm depends on the proportions of the energy counts as opposed to the volume of the energy counts. Further, the sorting algorithm can classify a piece of material from the recognition of a faint image of the spectral pattern of the piece.

Further, because x-rays are detected and an xrf spectrum is determined at a much faster rate, cumulatively, and because less x-rays are needed to classify a piece of material, pieces of materials as small as ¼ inch may be classified at rates fast enough to make the sorting and recycling of such pieces economically valuable. Size as used herein to describe the size of a piece of material means the largest diameter of the piece of material in any dimension.

A problem with known material sorting systems, where pieces of materials are conveyed along a conveyor belt, is that it is difficult to detect specific elements that fluoresce at low energy levels because the x-rays from these elements are so weak that the x-rays are absorbed by air before reaching a detector. For example, aluminum is difficult to detect because it fluoresces at energy levels below 2 kev, and these x-rays are mostly absorbed by air before reaching an x-ray detector. Although the proceeding example uses aluminum for illustrative purposes, the example applies analogously to other elements that fluoresce at low energy levels. One solution is to put the x-ray detector closer to the piece of material that includes the aluminum. However, when conveying pieces of materials of variable size along a conveyor belt, the x-ray detector must be kept at a distance sufficient to accommodate the largest possible size of a piece. Thus, small pieces may be further away from the x-ray detector than larger ones.

In an illustrative embodiment of a high speed sorting of materials, a piece of material comprising aluminum, or any element that fluoresces at low energy levels, may be classified by recognizing the spectral pattern of the material as a whole. For example, aluminum may be classified by the spectral pattern of its alloys by storing the spectral pattern of aluminum alloys as reference spectra, and mapping an air jet to each reference spectra. In an illustrative embodiment, if it is desired to sort all aluminum alloys into a common bin, multiple air jets may be mapped to a common sorting bin. The high speed material sorting process as described herein may be executed, and pieces of aluminum alloy may be recognized and sorted in accordance with the sorting algorithm.

In an illustrative embodiment of a high speed material sorting system, multiple sorting systems may be used in parallel, each sorting system optimized for a particular classifications of materials or particular piece sizes. For example: a first system may sort pieces of material having a size from approximately ¼ inch to approximately ⅝ inch; a second system may sort pieces having a size from approximately ⅝ inch to 4 inches; and a third system may sort pieces between 4 inches and 12 inches. Prior to sorting, a feedstock of materials could be pre-sorted into feedstocks, one for each size category. For each size-specific system, various parameters could be optimized for the size of the materials it sorts. Parameters that may be adjusted include: the width and length of the belt; the width and height of the chamber; the speed of the belt; the distance between the x-ray source and the detection area, the distance between the x-ray detector and the detection area; the power of the x-ray source resulting in the intensity of the irradiated x-rays; the resolution of the determined spectra; the reference spectra; the number of reference spectra; the threshold value for each spectra; the number of sorting bins; the mapping of reference spectra to sorting bins, etc.

In an illustrative embodiment of a high speed materials sorting system, multiple x-ray detectors may be used. Such x-ray detectors may be all be aimed at the same detection area, or may be aimed at different detection areas. The x-rays detected by the multiple detectors may all be caused by a common x-ray source or multiple x-ray sources, where the x-ray detectors may be placed in series along the path of the conveyor belt. Using multiple x-ray detectors allows for the gathering of more xrf to produce a more accurate spectral pattern of a piece of material, thus reducing the effects of random variations inherent with detecting x-rays.

In an illustrative embodiment of a high speed materials sorting system, materials may be sorted using a type of binary sort. For example, as opposed to the air jets 13-17 ejecting pieces of materials into sorting bins 18-22, the air jets can be used to eject the piece of materials onto additional conveyor belts that lead to additional sorting.

Figure 9:
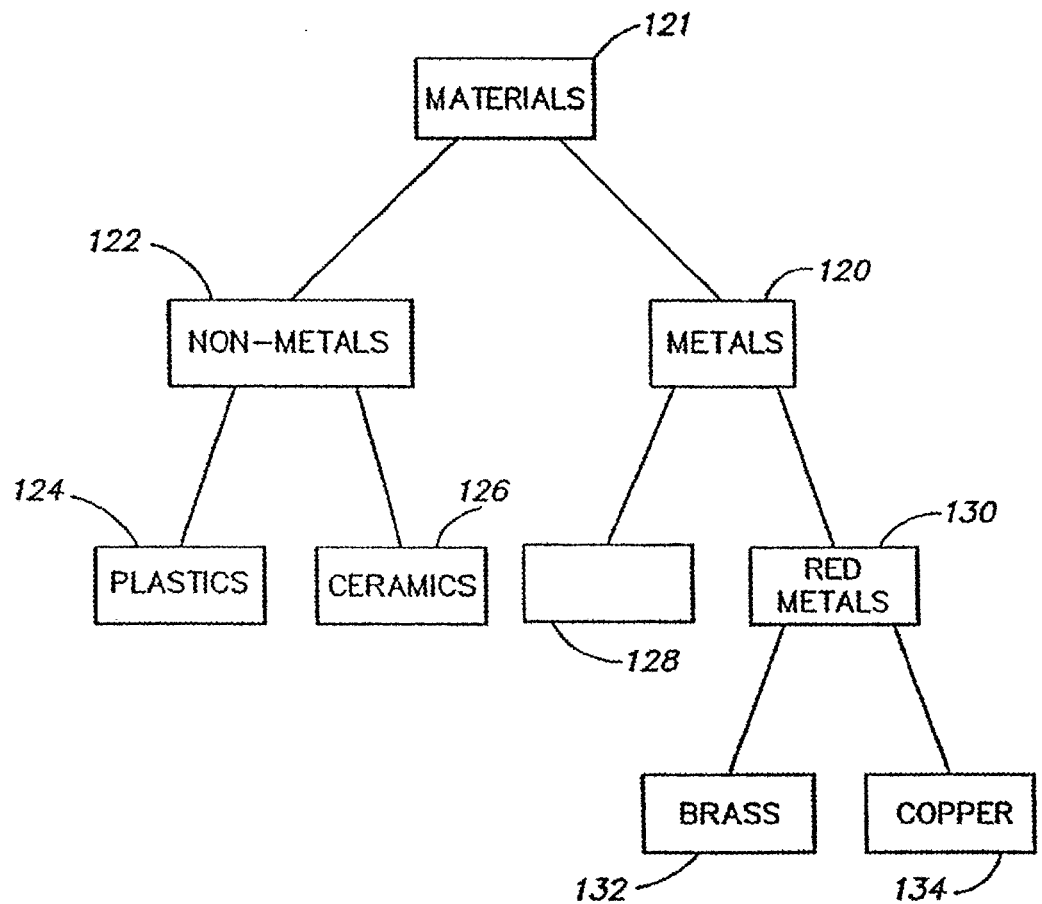
FIG. 9 is a block diagram showing an illustrative embodiment of a process of binary sorting materials.

FIG. 9 is a block diagram illustrating an example illustrative embodiment of a binary sort. In a first stage of the binary sort, materials may be sorted into metals 120 and non-metals 122 by a material sorting system such as, for example, the high speed material sorting system 1 of FIG. 1. The system may eject metals onto a first belt for conveying metals into a material sorting system for sorting metals, and eject non-metals onto a second belt for conveying non-metals into a material sorting system for sorting non-metals. To implement this first sort, the reference spectra of each sorting system and their respective threshold values may be selected such that the each sorting system is designed to differentiate between metals and non-metals. Selecting a proper threshold for a particular sort is described above with respect to the sorting algorithm.

In another stage of the binary sort, non-metals 122 may be sorted into plastics 124 and ceramics 126, while metals 120 may be sorted into red metals 130 and other metals 128. The red metals 130 may then be separated into copper 134 and brass 132. Each sort may be performed analogously to the process described above with respect to the first stage of the binary sort.

Figure 8:
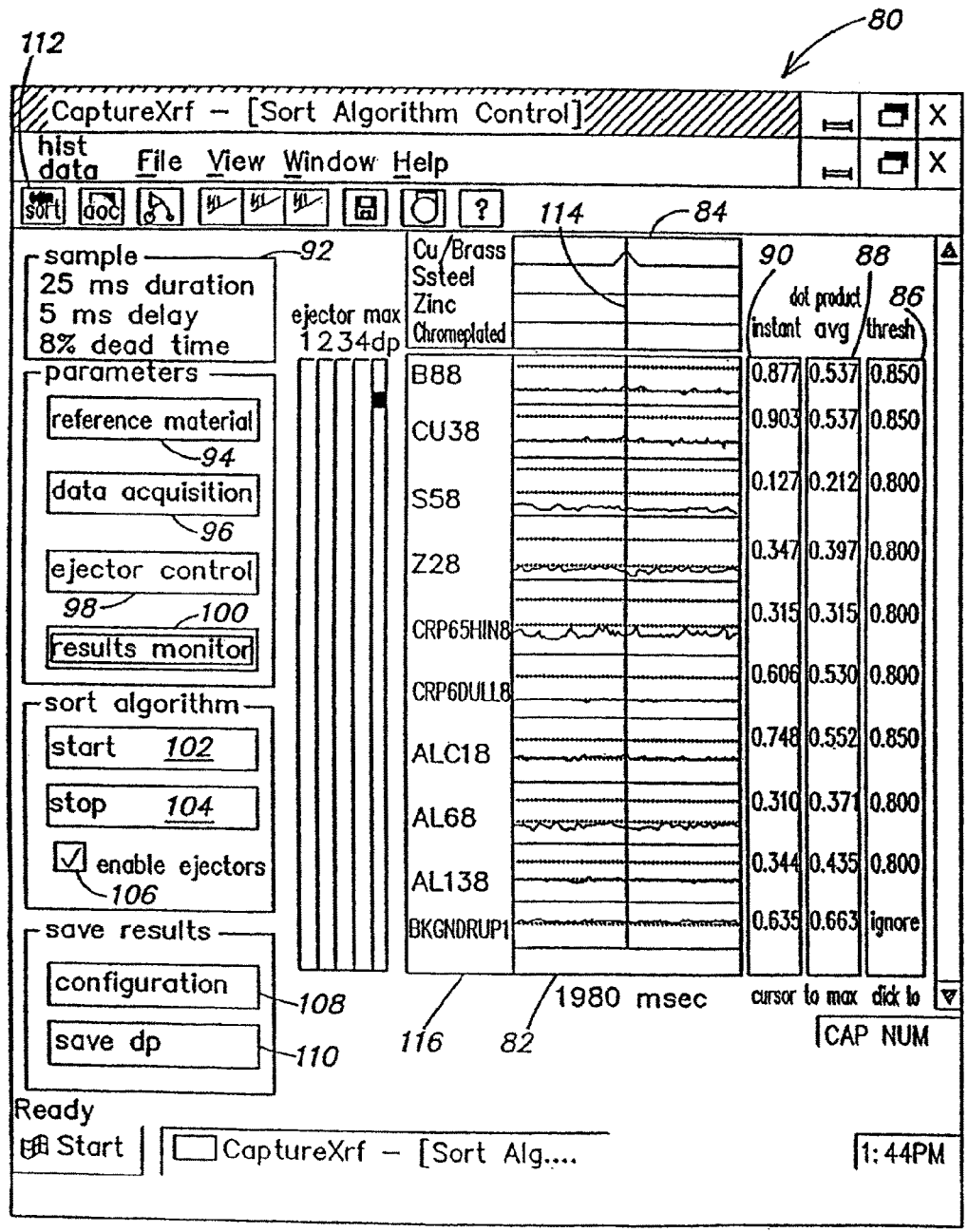
FIG. 8 is a screen capture of an illustrative embodiment of a user interface for analyzing detected x-ray fluorescence spectra.

FIG. 8 is a screen capture illustrating an illustrative embodiment of graphical display generated by a user interface 37. In an illustrative embodiment, the user interface 37 is a graphical application written with standard Microsoft tools and libraries and executes strictly in NT user space. Other known commercial tools and libraries may be used. The user interface functions for screen management, keyboard or mouse input, and file I/O may be supported by the standard WIN 32 libraries. This graphical application may run simultaneously with other applications, and may be executed (and task-swapped) by an NT task scheduler.

Although not shown in FIG. 4, an interface may be provided between the user interface 37 and the sorting application 35. This interface passes commands between the user interface 37 and the sorting application 35, and the sorting algorithm results are passed back for display by the user interface 37. A HyperKernel extension library may manage a shared-memory region that is used to exchange data between the user interface 37 (and user, or virtual memory space) and the real-time code (in kernel, or physical memory space) of the sorting application 35.

In this illustrative embodiment, the graphical display 80 includes buttons at the top and left of the screen that are used for program control, setting parameters, and database management. Reference material button 94 allows a system user to set parameters for reference materials. Data acquisition button 96 allows a user to set parameters for data acquisition. The ejector control button 98 allows a user to set parameters for controlling ejection via the air jets. Results monitor button 100 allows a system user to set parameters for monitoring the results of the sorting algorithm. Start button 102 permits a system user to start the sorting algorithm, while stop button 104 allows the system user to stop the sort algorithm. Check box 106 allows a user to enable or disable the ejectors. Configuration button 108 permits a system user to save the current configuration. Save dot product button 110 permits a system user to save the results of a dot product between the xrf spectral pattern of a detected material and the xrf spectral pattern of a reference material.

The histogram chart 82 displays a scrolling time histogram of dot product values taken with each reference spectra as a sample moves through the detection chamber 7. The numeric tables 86, 88, 90 on the right of the screen show dot product values and sorting threshold settings. The instant dot products table 90 shows the dot products between a detected material and a reference material at a point in time indicated by cursor 114, the cursor 114 being adjustable by a system user. The average dot product table 88 displays the average dot product across the time interval displayed in the histogram chart 82. The threshold table 86 indicates the threshold value for the corresponding reference material of the reference material column 116.

The ejection destination chart 84 identifies the air jet/sorting bin corresponding to the classification of the piece of material determined by the sorting algorithm. For example, in the histogram chart 82, the dot products of the highest value at the instant indicated by the cursor 114 is that of Cu 38 (copper), which, as indicated by the instant dot product table, has a dot product of 0.903. In accordance with this determination, the ejector designation chart shows that the Cu/brass (copper/brass) ejector has been designated for the piece of material.

The high-speed metal sorting system and method disclosed herein allows for hand shearing to be replaced by automated size reduction and sorting techniques such as shredding, grinding, crushing, air classification, eddy-current separation, magnetic separation, and screening. High-value metals, or other materials, can be liberated from non-metals or from lower value metals or materials to which they are adjoined. Once liberated and grouped by size, the particles may be singulated (particle by particle with spaces between particles) and fed onto conveyor belt 5.

The xrf processing module 9 may be implemented with a typical computer system. The invention is not limited to any specific computer described herein. Many other different machines may be used to implement the xrf processing module 9. Such a suitable computer system includes a processing unit which performs a variety of functions and a manner well-known in the art in response to instructions provided from an application program. The processing unit functions according to a program known as the operating system, of which many types are known in the art. The steps of an application program are typically provided in random access memory (RAM) in machine-readable form because programs are typically stored on a non-volatile memory, such as a hard disk or floppy disk. After a user selects an application program, it is loaded from the hard disk to the RAM, and the processing unit proceeds through the sequence of instructions of the application program.

The computer system also includes a user input/output (I/O) interface. The user interface typically includes a display apparatus (not shown), such as a cathode-ray-tube (CRT) display in an input device (not shown), such as a keyboard or mouse. A variety of other known input and output devices may be used, such as speech generation and recognition units, audio output devices, etc.

The computer system also includes a video and audio data I/O subsystem. Such a subsystem is well-known in the art and the present invention is not limited to the specific subsystem described herein. The audio portion of the subsystem includes an analog-to-digital (A/D) converter (not shown), which receives analog audio information and converts it to digital information. The digital information may be compressed using known compression systems, for storage on the hard disk to use at another time. A typical video portion of subsystem includes a video image compressor/decompressor (not shown) of which many are known in the art. Such compressor/decompressors convert analog video information into compressed digital information. The compressed digital information may be stored on hard disk for use at a later time.

One or more output devices may be connected to the computer system implementing the xrf processing module. Example output devices include a cathode ray tube (CRT) display, liquid crystal displays (LCD) and other video output devices, printers, communication devices such as a modem, storage devices such as disk or tape, and audio output. One or more input devices may be connected to the computer system. Example input devices include a keyboard, keypad, track ball, mouse, pen and tablet, communication device, and data input devices such as audio and video capture devices and sensors. The computer system is not limited to the particular input or output devices used in combination with the computer system or to those described herein.

The xrf processing module 9 may be implemented on a general purpose computer system which is programmable using a computer programming language, such as "C++," JAVA or other language, such as a scripting language or even assembly language. The computer system may also be specially programmed, special purpose hardware. In a general purpose computer system, the processor is typically a commercially available processor, such as the series x86 and Pentium processors, available from Intel, similar devices from AMD and Cyrix, the 680x0 series microprocessors available from Motorola, and the PowerPC microprocessor from IBM. Many other processors are available. Such a microprocessor executes a program called an operating system, of which WindowsNT, Windows95 or 98, UNIX, Linux, DOS, VMS, MacOS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory and tape are examples. The disk may be removable, for example, a floppy disk or a read/write CD, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk after processing is completed. A variety of mechanisms are known for managing data movement between the disk and the integrated circuit memory element, and the invention is not limited thereto. The invention is not limited to a particular memory system.

Such a system may be implemented in software or hardware or firmware, or a combination of the three. The various elements of the system, either individually or in combination may be implemented as a computer program product tangibly embodied in a machine-readable storage device for execution by a computer processor. Various steps of the process may be performed by a computer processor executing a program tangibly embodied on a computer-readable medium to perform functions by operating on input and generating output. Computer programming languages suitable for implementing such a system include procedural programming languages, object-oriented programming languages, and combinations of the two.

The xrf processing module is not limited to a particular computer platform, particular processor, or particular programming language. Additionally, the computer system may be a multi processor computer system or may include multiple computers connected over a computer network. Steps 61-69 of FIG. 6 may be separate modules of a computer program, or may be separate computer programs. Such modules may be operable on separate computers.

Additional Embodiments

In practice, instead of using a single detector, multiple x-ray detectors can be arrayed across a feed path to give readings of multiple items fed side-by-side along the feed path in order to increase throughput and/or decrease placement requirements. The x-ray detectors may sense fluorescence from items which are irradiated by a common excitation source or individual excitation sources. In this arrangement, it may be (but is not necessarily) preferable to perform a binary sort (as in the NRT VinylCycle) instead of sequential multiple sorts.

One of the surprise discoveries is that we found that aluminum samples from automobile scrap can be identified by the sorting system. This is an unexpected result that we did not earlier anticipate. Aluminum itself is not detectable by our experimental system since it fluoresces only a Ka emission at 1.49 kev and a Kβ emission and 1.55 kev. These low energy x-rays are readily absorbed in air before they can reach the detection system. Therefore, we had proposed that the unit could be used to detect the heavier nonferrous metals letting aluminum flow through undetected. However, when we looked at an aluminum sample with our detection system, we found a strong spectrum which we identified as belonging to the alloying metals in the aluminum.

In initial profiling of the aluminum samples, we noticed three types of alloys present in the samples. In order to test the ability of the system to recognize aluminum by alloy type we picked a representative sample from each of the three types to use as a reference material and generated a reference fluorescence spectrum from each of them. One of the reference spectra represented the predominant number of samples in our sample group. We went back into the original sample and selected an additional six samples having the other spectra so that we had twenty samples of one alloy type, AL13B, four samples of type AL6B, and four samples of type ALC1B. We then loaded the three reference spectra into a prototype sorter and ran the twenty-eight samples through the sorter five times each to determine if they could be identified by alloy type. We used the same system settings as for the earlier prior tests.

We found that our system had the ability to separate one non-ferrous metal from a group of metals, and also the ability to recover and sort one alloy of non-ferrous metals from all other alloys and groups of non-ferrous metals. This result can be extended to recovery of several different alloys at the same time by using multiple sensing and separation channels within a single machine. Technologies exist to identify non-ferrous metals and alloys, but they are slow. No rapid sorting technology is in existence today to accomplish sortation of metallic alloys. Thus, separation of alloys at rapid speeds represents an entirely new commercial opportunity.

Having now described some illustrative embodiments, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method steps or apparatus elements, it should be understood that those steps and those elements may be combined in other ways to accomplish the same objectives. Steps, elements and features discussed only in connection with one embodiment are not intended to be excluded from a similar role in other embodiments.

The invention claimed is:

1. A high-speed process for classifying a piece of material of unknown composition, the process comprising acts of:
   detecting fluoresced x-rays emitted by the piece with at least one x-ray detector in response to irradiation of the piece with incident x-rays;
   determining an x-ray fluorescence spectrum of the piece of material from the detected fluoresced x-rays, wherein the determined x-ray fluorescence spectrum has a spectral pattern;
   recognizing the spectral pattern of the determined x-ray fluorescence spectrum; and
   classifying the piece based on the recognition of the spectral pattern,
   wherein the acts of detecting, determining, recognizing and classifying are cumulatively performed in less than one second.

2. The high-speed process of claim 1, further comprising irradiating the piece with the incident x-rays, and wherein irradiating the piece with the incident x-rays comprises irradiating the piece using multiple x-ray sources.

3. The high-speed process of claim 1, wherein detecting the fluoresced x-rays with at least one x-ray detector comprises detecting the fluoresced x-rays with multiple x-ray detectors.

4. The high-speed process of claim 3, wherein the multiple x-ray detectors are placed in series.

5. The high-speed process of claim 4, further comprising conveying the piece along a conveyor, and wherein the multiple x-ray detectors are placed in series along a path of the conveyor.

6. The high-speed process of claim 3, further comprising disposing the piece on a conveyor side-by-side with other pieces to be classified and arranging the multiple x-ray detectors side-by-side across the conveyor.

7. The high-speed process of claim 1, wherein the piece is one of multiple pieces arranged side-by-side on a conveyor, and wherein the method further comprises:
irradiating each of the multiple pieces with x-rays; and
detecting x-rays fluoresced by each of the multiple pieces.

8. The high-speed process of claim 7, wherein detecting x-rays fluoresced by each of the multiple pieces comprises using multiple x-rays detectors.

9. The high-speed process of claim 8, wherein the multiple x-ray detectors are arranged side-by-side across the conveyor and wherein each of the x-ray detectors is configured to detect x-rays emitted by a corresponding one of the multiple pieces.

10. The high speed process of claim 7, further comprising:
determining an x-ray fluorescence spectrum of two or more of the multiple pieces from the detected fluoresced x-rays detected from the corresponding pieces, wherein each of the determined x-ray fluorescence spectra has a spectral pattern;
recognizing each spectral pattern; and
classifying each of the two or more of the multiple pieces based on the spectral patterns.

11. The high-speed process of claim 1, wherein the piece comprises aluminum, wherein the spectral pattern is indicative of alloying metals in the aluminum, and wherein classifying the piece based on the recognition of the spectral pattern comprises classifying the piece based on the alloying metals.

12. The high-speed process of claim 1, wherein the piece comprises an alloy of non-ferrous material, and wherein classifying the piece based on the recognition of the spectral pattern comprises classifying the piece as including the alloy of non-ferrous material.

13. The high-speed process of claim 1, wherein the piece is approximately ¼ inch in size.

14. The high-speed process of claim 1, wherein classifying the piece based on the recognition of the spectral pattern comprises classifying the piece as belonging to one of two potential classification groups.

15. The high-speed process of claim 14, wherein the piece is one of multiple pieces arranged side-by-side on a conveyor, and wherein the method further comprises:
irradiating each of the multiple pieces with x-rays; and
detecting x-rays fluoresced by each of the multiple pieces.

16. The high-speed process of claim 15, wherein detecting x-rays fluoresced by each of the multiple pieces comprises using multiple x-ray detectors.

17. The high-speed process of claim 16, wherein the multiple x-ray detectors are arranged side-by-side across the conveyor and wherein each of the x-ray detectors is configured to detect x-rays emitted by a corresponding one of the multiple pieces.

18. A system comprising:
a conveyor configured to convey pieces of material;
at least one x-ray source configured to generate incident x-rays and emit the incident x-rays toward the pieces of material as they are conveyed along the conveyor;
a plurality of x-ray detectors arranged across the conveyor, wherein each x-ray detector of the plurality of x-ray detectors is configured to detect x-ray fluorescence emitted by at least one of the pieces;
a spectrum acquisition module coupled to the plurality of x-ray detectors to receive outputs of the x-ray detectors and to produce multiple x-ray fluorescence spectra, each x-ray fluorescence spectrum of the multiple x-ray fluorescence spectra corresponding to one of the x-ray detectors; and
a classification module configured to receive the x-ray fluorescence spectra and to generate at least one output corresponding to each x-ray fluorescence spectrum of the x-ray fluorescence spectra, the at least one output representing at least one classification signal based on one or more energy levels within the corresponding x-ray fluorescence spectrum;
wherein the plurality of x-ray detectors, the spectrum acquisition module, and the classification module are operative in combination to detect the x-ray fluorescence emitted by the at least one of the pieces, produce the x-ray fluorescence spectra, and generate the at least one output corresponding to each x-ray fluorescence spectrum in a combined time of less than one second.

* * * * *